United States Patent
Rothstein

(10) Patent No.: US 6,291,213 B1
(45) Date of Patent: *Sep. 18, 2001

(54) METHOD FOR GENERATING A DIRECTED, RECOMBINANT FUSION NUCLEIC ACID

(75) Inventor: Rodney Rothstein, Maplewood, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/312,731

(22) Filed: May 14, 1999

Related U.S. Application Data

(63) Continuation of application No. PCT/US97/20755, filed on Nov. 13, 1997, which is a continuation-in-part of application No. 08/746,667, filed on Nov. 14, 1996, now Pat. No. 5,942,422.

(51) Int. Cl.[7] .............. C12P 19/34; C12P 21/06; C12Q 1/68; C12N 15/11

(52) U.S. Cl. .............. 435/91.2; 435/6; 435/69.1; 435/91.1; 435/252.3; 536/23.1; 536/25.3

(58) Field of Search ................ 435/91.1, 91.2, 435/6, 69.1, 252.3; 536/23.1, 25.3

(56) References Cited

U.S. PATENT DOCUMENTS 5,942,422 * 8/1999 Rothstein .................. 435/91.1

OTHER PUBLICATIONS

Jones et al. "DNA mutagenesis and recombination" Apr. 19, 1990, Nature, 344: 793–794.*

* cited by examiner

Primary Examiner—Stephanie W. Zitomer
Assistant Examiner—B J Forman
(74) Attorney, Agent, or Firm—John P. White; Cooper & Dunham LLP

(57) ABSTRACT

The present invention provides for a method for generating a fusion nucleic acid molecule capable of cross-over recombination which comprises: (a) contacting a first pair of primers with a first strand and a second strand of a first nucleic acid molecule and a second pair primers with a first strand and a second strand of a second nucleic acid molecule wherein the primers are suitable for use in a polymerase chain reaction; (b) amplifying the first nucleic acid molecule and the first pair of primers and the second nucleic acid molecule and the second pair of primers under amplification conditions, separately; (c) mixing the amplification products from step (b) and the first primer of the first pair of primers and the second primer of the second pair of primers under hybridization conditions; (d) amplifying the hybridized molecules of step (c) under amplification conditions so as to generate a directed, recombinant fusion nucleic acid molecule capable of cross-over recombination.

17 Claims, 25 Drawing Sheets

FIGURE 5

Adaptamer A₁
```
      R   G   S   E   F   Q   Q   E   F   G   T   R
5'-cga gga tcc gaa ttc cag CAA GAA TTC GGC ACG AGG-3'
```

Adaptamer A₂
```
      R   G   S   E   F   Q   P   R   I   R   H   E
5'-cga gga tcc gaa ttc cag cCA AGA ATT CGG CAC GAG G-3'
```

Adaptamer A₃
```
      R   G   S   E   F   Q   A   K   N   S   A   R
5'-cga gga tcc gaa ttc cag gcC AAG AAT TCG GCA CGA GG-3'
```

Adaptamer B

5'-gttgaagtgaacttgcggGACGTTGTAAAACGACGG-3'

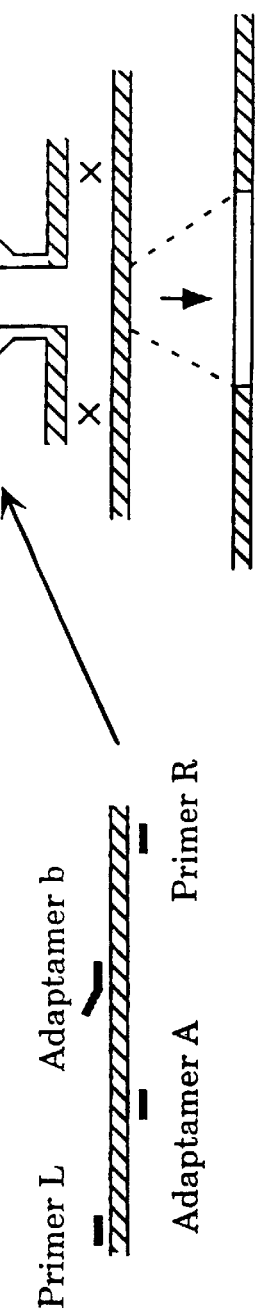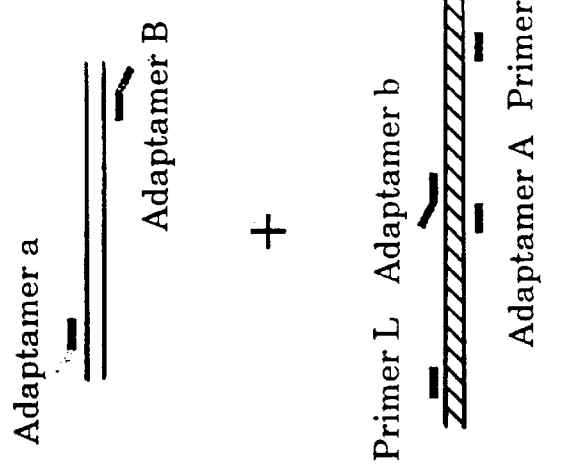
FIGURE 14A
FIGURE 14B

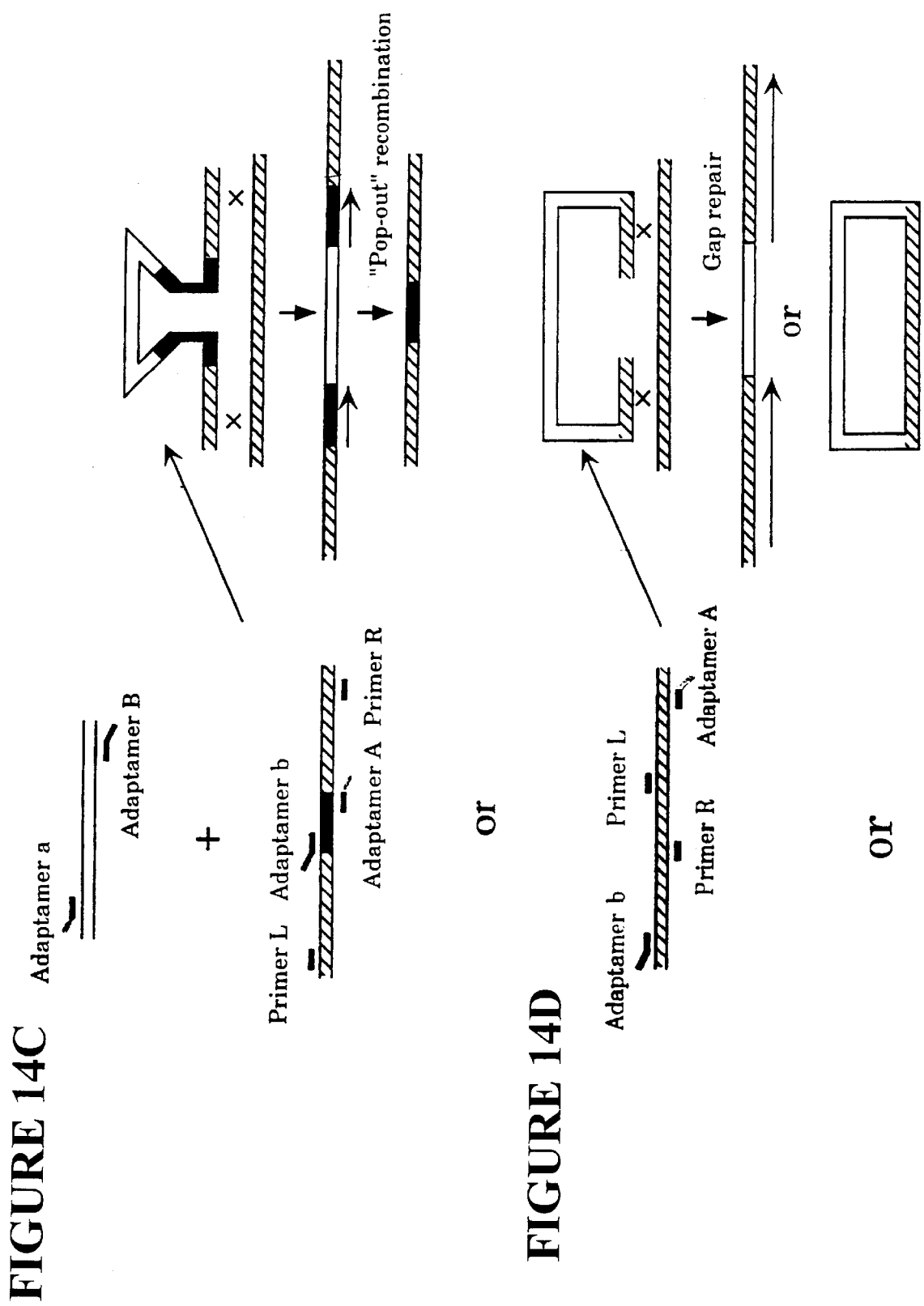

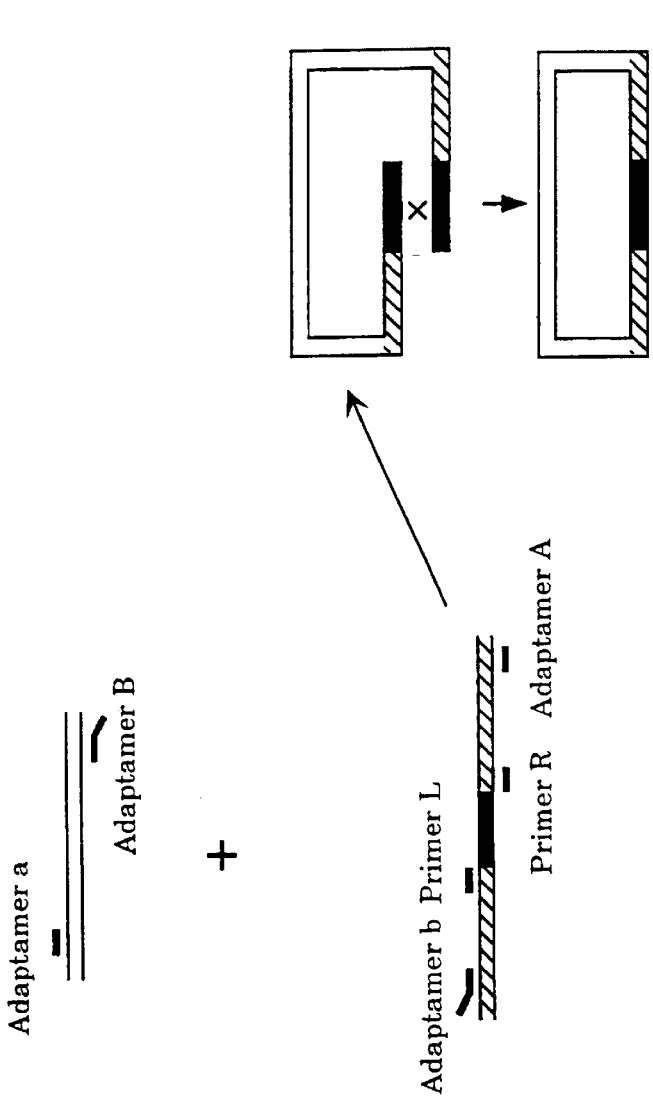
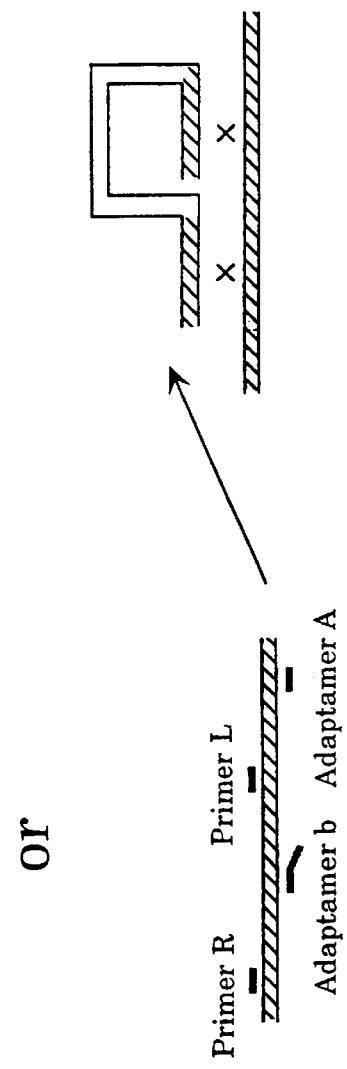
FIGURE 14E
FIGURE 14F

Also

Fusion fragment

METHOD FOR GENERATING A DIRECTED, RECOMBINANT FUSION NUCLEIC ACID

This application is a continuation of PCT International Application No. PCT/US97/20755, filed Nov. 13, 1997, designating the United States of America, which was a continuation-in-part of U.S. Ser. No. 08/746,667 now U.S. Pat. No. 5,942,422 filed Nov. 14, 1996, the contents of which are hereby incorporated by reference into the present application.

A portion of the invention disclosed herein was made with Government support under NIH Grant No. GM50327 from the Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Attention of research scientists has recently focused upon various methods of creating libraries. The use of libraries is widespread in research and in the pharmaceutical industry. Libraries may consist of nucleic acid, peptides or even virtual molecules on a computer-readable material. Methods for the creation of libraries that are representative of the desired entity and that are useable has been a long felt challenge. In general, library construction has entailed many steps before the production of a final, useable library.

The following U.S. Patents are hereby incorporated by reference into this application in order to more fully describe the state of the art as known to one of ordinary skill in the art. U.S. Pat. No. 5,498,530, Peptide Library and Screening Method; U.S. Pat. No. 5,491,074 Association Peptides; U.S. Pat. No. 5,432,018 Peptide Library and Screening Systems; U.S. Pat. No. 5,427,908 Recombinant Library Screening Methods; U.S. Pat. No. 5,338,665 Peptide Library and Screening Method; U.S. Pat. No. 5,270,170 Peptide Library and Screening Method; U.S. Pat. No. 5,541,061 Methods for Screening Factorial Chemical Libraries; U.S. Pat. No. 5,482,845, Method for Construction of Normalized cDNA Libraries; U.S. Pat. No. 5,512,463, Enzymatic inverse polymerase chain reaction library mutagenesis.

There are also peptide libraries and chimeric libraries that have been described. For example, see U.S. Pat. No. 5,525,486, Process for constructing cDNA library, and novel polypeptide and DNA coding for the same; U.S. Pat. No. 5,565,332, Production of chimeric antibodies—a combinatorial approach; U.S. Pat. No. 5,521,077, Method of Generating Multiple Protein Variants and Populations of Protein Variants Prepared thereby; U.S. Pat. No. 5,324,663, Methods and Products for the Synthesis of oligosaccharide structure on glycoproteins, glycolipids, or as free molecules, and for the isolation of cloned genetic sequences that determine these structures.

There have been combinatorial libraries also described which are usually composed of organic molecules attached to a solid support. A recent description of recently published patent applications may be found in Nature Biotechnology, Vol 14:1028–1029. Therein, the following published patent applications and patents were listed and described: Patent No. GB 2295152 A, solid phase synthesis of chemical library on flat solid support sheets divided into identifiable reaction zones; WO 9612014 A, repertoire of oligonucleotide tags comprise molecular tagging system used to track identify and sort molecules; WO 9607754, Oligonucleotides for inducing mutagenesis in an Ig light chain CDR; WO 9603424 A, combinatorial library comprising Diels-Alder products easily functionalized to form peptidomimetics for treating, e.g. Parkinson's disease; WO 9603418 A, Soluble combinatorial library by solid phase synthesis by using soluble polymeric support for core molecule attachment and buildup; WO 9603212 A, multidimensional device for synthesis of combinatorial chemical libraries comprising stacked trays of synthesis cells supplied with substrates and reagents.

SUMMARY OF THE INVENTION

The present invention provides for a method for generating a directed, recombinant fusion nucleic acid molecule which comprises: (a) contacting a first pair of single-stranded primers with a first strand and a second strand of a first nucleic acid molecule and a second pair of single-stranded primers with a first strand and a second strand of a second nucleic acid molecule under hybridization conditions, wherein the primers are suitable for use in a polymerase chain reaction, and (i) the first primer of the first pair of primers comprises a sequence that is homologous to the first strand of the first nucleic acid molecule; (ii) the second primer of the first pair of primers comprises a 3' sequence that is homologous to the second strand of the first nucleic acid molecule and a 5' sequence; (iii) the first primer of the second pair of primers comprises a 3' sequence homologous to the first strand of the second nucleic acid molecule and a 5' sequence that is complementary to the 5' sequence of the second primer of the first pair of primers, and (iv) the second primer of the second pair of primers comprises a sequence that is homologous to the second strand of the second nucleic acid molecule; (b) amplifying the first nucleic acid molecule and the first pair of primers and the second nucleic acid molecule and the second pair of primers under amplification conditions, separately; (c) mixing the amplification products from step (b) and the first primer of the first pair of primers and the second primer of the second pair of primers under hybridization conditions; (d) amplifying the hybridized molecules of step (c) under amplification conditions so as to generate a directed, recombinant fusion nucleic acid molecule.

BRIEF DESCRIPTION OF THE FIGURES

FIG. 5. Four adaptamers are shown for generating EST fragments from sequences cloned in pT7T3D. For all four, the first 18 lower case letters are sequences homologous to pGAD10. For adaptamer $A_1$, (Seq. I.D. No. 1) the next 18 upper case letters are homologous to the EcoRI linker added to the cDNAs before cloning into the pT7T3D vector used by I.M.A.G.E. Adaptamer $A_2$ (Seq. I.D. No. 2)and adaptamer $A_3$ (Seq. I.D. No. 3) have one and two extra nucleotides, respectively between this sequence. The 18 upper case letters in adaptamer B (Seq I.D. No. 4) are homologous to sequences adjacent to the NotI linker used to prime the synthesis of the cDNA. After PCR with this set of adaptamers, one of the three will result in an in-frame fusion to the EST. The amino acids displayed above the nucleotide sequences of Adaptamers $A_1$, $A_2$ and $A_3$ represent the linker between the EST and the activation domain of Gal4 after successful recombination cloning.

FIGS. 14A, 14B, 14C, 14D, 14E and 14F. Description of some possible uses of adaptamers in the generation of directed, fusion recombinant nucleic acid molecules. There exist other uses of the adaptamers and the generation of directed, fusion recombinant nucleic acid molecules which are not depicted here.

FIG. 14A. Insertion. The use of adaptamers to orient and insert a foreign piece of nucleic acid into a region of an existing target nucleic acid. A first PCR of the foreign piece of nucleic acid and appropriate adaptamers is done in order to generate a product with ends receptive to overlap and connectivity with the target nucleic acid. The target nucleic acid is separately hybridized to two sets of primers as shown which are also adaptamers with complementary 5' sequences to the adaptamers used with the foreign nucleic acid. Adaptamer b and adaptamer A are predefined so that the 3' sequence of adaptamer b is complementary to the target nucleic acid adjacent to the region which is complementary to the 3' sequence of adaptamer A. Thus, the products from both PCRS may be mixed and again undergo PCR in order to generate the striped-&-white block product shown on the right of the figure. This product can then be mixed with the target nucleic acid under appropriate recombination conditions. Recombination would then occur and produce the final product shown: the target nucleic acid with the foreign nucleic acid inserted in the predetermined region. The region of insertion may be determined a priori and the adaptamers can be engineered based on the sequences surrounding the predefined insertion point.

FIG. 14B. Simultaneous insertion and deletion. The foreign nucleic acid is hybridized with predefined adaptamers as shown and described above. However, the 5' end sequence of the adaptamers are now engineered to reflect two sequences of the target nucleic acid some distance from each other.

FIG. 14C. An insertion accompanied by a duplication is depicted. Such a product may be obtained if the sequences projected for amplification from each pair of primers (primer L/adaptamer A and adaptamer b/primer R) cross one another upon amplification. The black box in the left hand drawing is the region that would be amplified by both sets of primers. The black boxes on the right side of the arrow indicate the same region shown as a duplication after the first recombination event. The white region depicts the foreign nucleic acid as in FIGS. 14A and 14B above. After the first recombination event, a second event (depicted "pop-out" recombination) can generate a single black region.

FIG. 14D. Gap repair. In this case, the engineering of the predefined adaptamers can create a gap or anomaly in the target sequence which can subsequently be repaired into a linear duplication or an intact circle.

FIG. 14E. Another example of engineered adaptamers used to create a duplication on the ends of the molecule such that recombination results in a circular molecule. FIG. 14F. Another example of engineered adaptamers to carry out recombination that results one or two linear molecules whose ends include the amplified sequences.

(FIG. 22A) When the mutation is close to the 3' end of a large gene (>2.5 kb), a new adaptamer $A^{int}$ is needed to amplify the 3' portion of the ORF. After amplification using adaptamer $A^{int}$ and adaptamer B, the fragment is fused to K. lactis URA3 fragments and co-transformed into yeast as described in FIGS. 19 and 20. Integration results in a full-length ORF only in the left copy following recombination that fuses the promoter (purple box labelled "Pro") and the endogenous, non-amplified region of the ORF (gray box) with the duplicated 3' amplified fragment (open box). The fragment on the right is truncated upstream of the sequence homologous to adaptamer $A^{int}$. (FIG. 22B) When the mutation is close to the 5' end in long essential genes, allele transfer requires two new adaptamers. Adaptamer $A^{pro}$ and adaptamer $B^{int}$ are used to amplify the 5' portion of the ORF including the promoter. After fusion to K. lactis URA3 and co-transformation (FIGS. 19 & 20), integration results in the generation of the full-length ORF with its promoter in the right repeat. The left copy contains a 3' truncation downstream of the sequence homologous to adaptamer $B^{int}$.

DETAILED DESCRIPTION OF THE INVENTION

Figure 1:
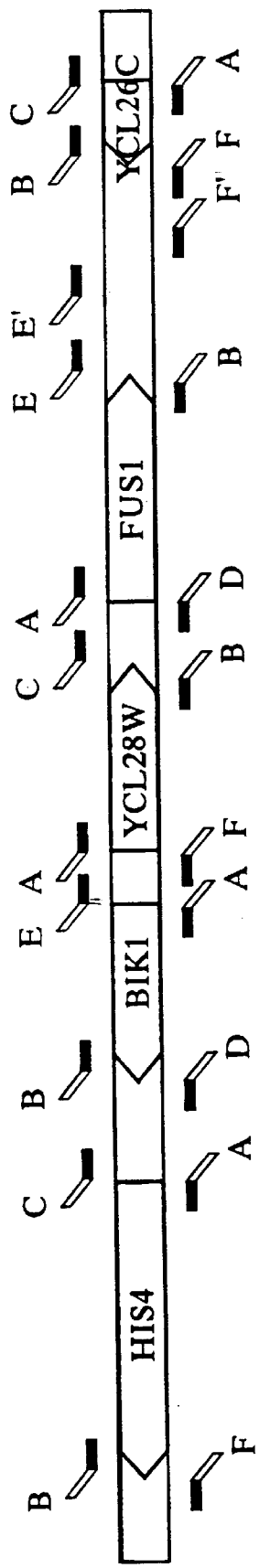
FIG. 1. A sample region of the yeast genome is shown. Arrows indicate open reading frames (ORFs) and the direction of transcription. YCL26C is 357 base pairs in length. The length of the adaptamers shown are not to scale.

The present invention provides for a method for generating a directed, recombinant fusion nucleic acid molecule which comprises: (a) contacting a first pair of single-stranded primers with a first strand and a second strand of a first nucleic acid molecule and a second pair of single-stranded primers with a first strand and a second strand of a second nucleic acid molecule under hybridization conditions, wherein the primers are suitable for use in a polymerase chain reaction, and (i) the first primer of the first pair of primers comprises a sequence that is homologous to the first strand of the first nucleic acid molecule; (ii) the second primer of the first pair of primers comprises a 3' sequence that is homologous to the second strand of the first nucleic acid molecule and a 5' sequence; (iii) the first primer of the second pair of primers comprises a 3' sequence homologous to the first strand of the second nucleic acid molecule and a 5' sequence that is complementary to the 5' sequence of the second primer of the first pair of primers, and (iv) the second primer of the second pair of primers comprises a sequence that is homologous to the second strand of the second nucleic acid molecule; (b) amplifying the first nucleic acid molecule and the first pair of primers and the second nucleic acid molecule and the second pair of primers under amplification conditions, separately; (c) mixing the amplification products from step (b) and the first primer of the first pair of primers and the second primer of the second pair of primers under hybridization conditions; (d) amplifying the hybridized molecules of step (c) under amplification conditions so as to generate a directed, recombinant fusion nucleic acid molecule.

The method may be repeated and the directed, recombinant fusion nucleic acid molecule generated may include another first nucleic acid molecule. The first nucleic acid molecule may include a cDNA molecule, a genomic nucleic acid molecule, a mitochondrial nucleic acid molecule, a chromosomal nucleic acid molecule, a synthetic nucleic acid molecule or an extra-chromosomal nucleic acid molecule. The first nucleic acid molecule may be derived from an mRNA, a single-stranded DNA, a biological sample or a single-stranded cDNA. The biological sample may include cerebrospinal fluid, blood, plasma, ascites fluid, tissue, urine, sputum, feces, hair, amniotic fluid, saliva, lung lavage, or cell extracts.

Each primer may include from about 4 nucleotides in length to about 200 nucleotides in length. Each primer may include from about 25 nucleotides in length to about 80 nucleotides in length. The first or second nucleic acid molecule or the primers may be synthesized de novo.

The present invention also provides for a method for generating a directed, recombinant fusion nucleic acid molecule capable of cross-over recombination which comprises: (A) contacting (i) a first pair of single-stranded primers with a first strand and a second strand of a first nucleic acid molecule, and (ii) a first single-stranded primer of a second pair of primers with a second nucleic acid molecule having two ends, wherein a first end is homologous to a portion of a fourth double-stranded nucleic acid molecule; (iii) a second single-stranded primer of the second pair of primers with a third nucleic acid molecule having two ends, wherein a first end is homologous to a second portion of the fourth double-stranded nucleic acid molecule, wherein the first and second pair of primers are suitable for use in a polymerase chain reaction, and (a) the first primer of the first pair comprises a 3' sequence that is homologous to the first strand of the first nucleic acid molecule and a 5' sequence that is homologous to the second end of the second double-stranded nucleic acid molecule; (b) the second primer of the first pair of primers comprises a 3' sequence that is homologous to the second strand of the first nucleic acid molecule and a 5' sequence that is homologous to the second end of the third double-stranded nucleic acid molecule; (c) the first primer of the second pair of primers comprises a sequence that is homologous to a first strand within the first end of the second nucleic acid molecule, and (d) the second primer of the second pair of primers comprises a sequence that is homologous to the second strand within the first end of the third nucleic acid molecule; (B) amplifying the first nucleic acid molecule and the first pair of primers, and the second and third nucleic acid molecules and the second pair of primers under amplification conditions so as to generate a directed, recombinant fusion nucleic acid molecule capable of cross-over recombination with the fourth double-stranded nucleic acid.

The method may be repeated and the directed, recombinant fusion nucleic acid molecule generated comprises another first nucleic acid molecule. The first nucleic acid molecule may include a cDNA molecule, a genomic nucleic acid molecule, a mitochondrial nucleic acid molecule, a chromosomal nucleic acid molecule, a synthetic nucleic acid molecule or an extra-chromosomal nucleic acid molecule. The first nucleic acid molecule may be derived from an mRNA, a single-stranded DNA, a biological sample or a single-stranded cDNA. The fourth nucleic acid molecule may include a replicable vector. The replicable vector may include a retroviral vector, a phage vector, an expression vector, a self-replicating vector, a viral vector, a plasmid vector, a phagemid vector, or a YAC vector. The second and the third nucleic acid molecules may be synthesized de novo.

The present invention may also provide for a method for generating a directed, recombinant fusion nucleic acid molecule capable of cross-over recombination which comprises: (A) contacting (i) a first pair of single-stranded primers with a first strand and a second strand of a first nucleic acid molecule; (ii) a second and a third pair of primers with a second nucleic acid molecule having a first strand and a second strand, wherein the primers are suitable for use in a polymerase chain reaction, and (a) the first primer of the first pair comprises a 3' sequence that is homologous to the first strand of the first nucleic acid molecule and a 5' sequence; (b) the second primer of the first pair of primers comprises a 3' sequence that is homologous to the second strand of the first nucleic acid molecule and a 5' sequence;(c) the first primer of the second pair of primers comprises a sequence that is homologous to the second strand of the second nucleic acid molecule; (d) the second primer of the second pair of primers comprises a 3' sequence that is homologous to the first strand of the second nucleic acid molecule and a 5' sequence that is complementary to the 5' sequence of the first primer of the first pair of primers; (e) the first primer of the third pair of primers comprises a 5' sequence complementary to the 5' sequence of the second primer of the first pair of primers and a 3' sequence homologous to the second strand of the second nucleic acid molecule, and (f) the second primer of the third pair of primers comprises a sequence that is homologous to the first strand of the second nucleic acid molecule; (B) amplifying (1) the first nucleic acid molecules and the first pair of primers and (2) the second nucleic acid molecule and the second and third pairs of primers, so as to generate at least one linear double-stranded nucleic acid product from each reaction; (C) denaturing the products from step (B) so as to obtain single-stranded products; (D) contacting the single-stranded products from step (C) with the first primer of the second set of primers and the second primer from the third set of primers, under suitable hybridization conditions, and (E) amplifying the the single-stranded products from step (D) under suitable amplification conditions, so as to generate a fusion nucleic acid molecule capable of cross-over recombination.

The cross-over recombination may occur in an appropriate host cell. The host cell may include a yeast cell, a mammalian cell, an *E.coli* cell, a eukaryotic cell, a prokaryotic cell., a plant cell, an insect cell, a slime mold cell. The first nucleic acid molecule may include a cDNA molecule, a genomic nucleic acid molecule, a mitochondrial nucleic acid molecule, a chromosomal nucleic acid molecule, a synthetic nucleic acid molecule or an extra-chromosomal nucleic acid molecule. The second nucleic acid molecule may include a replicable vector. The replicable vector may include a retroviral vector, a phage vector, an expression vector, a self-replicating vector, a viral vector, a plasmid vector, a phagemid vector, or a YAC vector. The fusion nucleic acid may include an insertion, a deletion a duplication or a mutation in the fusion nucleic acid molecule.

The present invention provides for a method for generating a directed, recombinant nucleic acid library which comprises: (A) contacting (i) a first pair of single-stranded primers with a first strand and a second strand of a first nucleic acid molecule; (ii) a second and a third pair of primers with a second nucleic acid molecule having a first strand and a second strand, wherein the primers are suitable for use in a polymerase chain reaction, and (a) the first primer of the first pair comprises a 3' sequence that is homologous to the first strand of the first nucleic acid molecule and a 5' sequence; (b) the second primer of the first pair of primers comprises a 3' sequence that is homologous to the second strand of the first nucleic acid molecule and a 5' sequence; (c) the first primer of the second pair of primers comprises a sequence that is homologous to the second strand of the second nucleic acid molecule; (d) the second primer of the second pair of primers comprises a 3' sequence that is homologous to the first strand of the second nucleic acid molecule and a 5' sequence that is complementary to the 5' sequence of the first primer of the first pair of primers; (e) the first primer of the third pair of primers comprises a 5' sequence complementary to the 5' sequence of the second primer of the first pair of primers and a 3' sequence homologous to the second strand of the second nucleic acid molecule, and (f) the second primer of the third pair of primers comprises a sequence that is homologous to the first strand of the second nucleic acid molecule; (B) amplifying (1) the first nucleic acid molecule and the first pair of primers and (2) the second nucleic acid molecule and the second and third pairs of primers, so as to generate at least one linear double-stranded nucleic acid product from each reaction; (C) denaturing the products from step (B) so as to obtain single-stranded products; (D) contacting the single-stranded products from step (C) with the first primer of the second set of primers and the second primer from the third set of primers under suitable hybridization conditions, and (E) amplifying the the single-stranded products from step (D) so as to generate a fusion nucleic acid molecule capable of cross-over recombination under suitable amplification conditions; (F) mixing the fusion nucleic acid molecule with the second nucleic acid molecule under suitable recombination conditions so as to generate a directed, recombinant nucleic acid library.

The library may include a two-hybrid library, an interaction library, a receptor library, a whole animal library, a tagged library, a chimeric library, a gene fusion library, a promoter trap library, an expression library, or a mutagenesis library.

The cross-over recombination may occur in an appropriate host cell. The host cell may include a yeast cell, a mammalian cell, an *E.coli* cell, a eukaryotic cell, a prokaryotic cell, a plant cell, an insect cell, a slime mold cell.

The present invention also may include a kit for generating a fusion nucleic acid based library which comprises: (a) a plurality of the adapted nucleic acid molecule primers of claim 9; (b) reagents suitable to carry out a plurality of polymerase chain reactions, and (c) a replicable vector suitable for recombination.

The present invention provides for a method for generating a directed, recombinant fusion nucleic acid molecule capable of cross-over recombination which comprises: (A) providing for:(i) a first double-stranded nucleic acid molecule having a first strand and a second strand; (ii) a second double-stranded nucleic acid molecule having two ends, wherein a first end is homologous to a portion of a fourth double-stranded nucleic acid molecule; (iii) a third double-stranded nucleic acid molecule having two ends, wherein a first end is homologous to a second portion of the fourth double-stranded nucleic acid molecule; (iv) a first pair of primers and a second pair of primers suitable for use in a polymerase chain reaction, wherein, (a) a first primer of the first pair comprises a 3' sequence that is complementary to the first strand of the first nucleic acid molecule and a 5' sequence that is homologous to the second end of the second double-stranded nucleic acid molecule; (b) a second primer of the first pair of primers comprises a 3' sequence that is complementary to the second strand of the first nucleic acid molecule and a 5' sequence that is homologous to the second end of the third double-stranded nucleic acid molecule; (c) the first primer of the second pair of primers comprises a sequence that is complementary to a first strand within the first end of the second nucleic acid molecule, and (d) the second-primer of the second pair of primers comprises a sequence that is complementary to the second strand within the second end of the third nucleic acid molecule; (B) performing extension, denaturation and hybridization steps of a polymerase chain reaction to generate at least one linear product from a mixture of the first, second and third nucleic acid molecules and the first and second pairs of primers so as to generate a directed, recombinant fusion nucleic acid molecule capable of cross-over recombination with the fourth double-stranded nucleic acid.

A method for generating a directed, recombinant fusion nucleic acid molecule capable of cross-over recombination which comprises: (A) providing for: (i) a first double-stranded nucleic acid molecule having a first strand and a second strand; (ii) a second double-stranded nucleic acid molecule having a first strand and a second strand; (iii) three pairs of primers suitable for use in a polymerase chain reaction, wherein, (a) a first primer of the first pair comprises a 3' sequence that is complementary to the first strand of the first nucleic acid molecule and a 5' sequence; (b) a second primer of the first pair of primers comprises a 3' sequence that is complementary to the second strand of the first nucleic acid molecule and a 5' sequence; (c) the first primer of the second pair of primers comprises a sequence that is complementary to the second strand of the second nucleic acid molecule, and (d) the second primer of the second pair of primers comprises a 3' sequence that is complementary to the first strand of the second nucleic acid molecule and a 5' sequence that is homologous the 5' sequence of the first primer of the first pair of primers; (e) a first primer of the third pair of primers comprises a 5' sequence homologous to the 5' sequence of the second primer of the first pair of primers and a 3' sequence complementary to the second strand of the second nucleic acid molecule; (f) a second primer of the third pair of primers comprises a sequence that is complementary to the first strand of the second nucleic acid molecule; (B) performing extension, denaturation and hybridization steps of two polymerase chain reactions separately, comprising either: (1) the first and second nucleic acid-molecules and the first and second pairs of primers and (2) the third nucleic acid molecule and the third pair of primers, or (3) the first and third nucleic acid molecules and the first and third pairs of primers and (4) the second nucleic acid molecule and the second pair of primers, so as to generate at least one linear nucleic acid product from each reaction; (C) performing extension, denaturation and hybridization steps of a polymerase chain reaction with the products from step (B) and the first primer of the second set of primers and the second primer from the third set of primers so as to generate a fusion nucleic acid molecule capable of cross-over recombination.

The present invention provides for the treatment of a nucleic acid sample or a biological sample to denature the double-stranded nucleic acid molecules and cause such hydrogen-bonded double-stranded molecules to become single-stranded. Such denaturing conditions may be heat, solvent, salt. The resulting nucleic acid molecules are then contacted with single-stranded oligonucleotide primers, the primers being capable of specifically hybridizing with predefined regions of the nucleic acid molecule and the primers being of a predefined sequence that is homologous to portions of other primers, under hybridizing conditions. Then, any nucleic acid molecules to which a pair of primers hybridizes are amplified so as to obtain a double-stranded amplification product. The amplification product may then be used in another denaturation and hybridization step with other nucleic acid molecules nd primers so as to produce a fusion, recombinant nucleic acid molecule.

Appropriate reaction conditions sufficient to permit specific hybridization and application through the following cycle include: denaturing the nucleic acid sequence; adding the primers and allowing them to hybridize to the appropriate strand of nucleic acid, primer extension products are formed from the primers and the nucleoside triphosphates, the extension products separate from the strands to become templates for the primers and new primer extension products are formed, wherein the hybridization, extension, and separation in the cycle occur at the appropriate temperature. (See U.S. Pat. No. 5,569,582, Rapid Amplification and Detection of Nucleic Acids.)

As used herein "amplification conditions" are those conditions under which a nucleic acid molecule may hybridize with two oligonucleotide primers which have some homology to the nucleic acid molecule and through primer extension replicate the nucleic acid molecule making a single-stranded nucleic acid molecule into a double stranded nucleic acid molecule via primer extension. This is elongation. The two strands are then melted apart by raising of the temperature and the single strands are again available for hybridization with a homologous single stranded oligonucleotide primer. Such conditions are well known to one of ordinary skill in the art and are described in more detail for certain specific nucleic acid molecules hereinbelow.

As used herein, "hybridization conditions" includes those temperatures, salt concentrations, primer sequences, nucleic acid sequences, solvent concentrations that allow two single-stranded nucleic acid molecules to base pair via hydrogen bonding as described by Watson and Crick. These conditions will be specific to each set of nucleic acids and primers. However, general conditions are well known to one of skill in the art and are described and referenced more fully hereinbelow.

As used herein "PCR" refers to a process of amplifying one or more specific nucleic acid sequences, wherein (1) oligonucleotide primers which determine the ends of the sequences to be amplified are annealed to single-stranded nucleic acid, (2) a nucleic acid polymerase extends the 3' ends of the annealed primers to create a nucleic acid strand complementary in sequence to the nucleic acid to which the primers were annealed, (3) the resulting double-stranded nucleic acid is denatured to yield two single-stranded nucleic acids, and (4) the processes of primer annealing, primer extension, and product denaturation are repeated enough times to generate easily identified and measured amounts of the sequences defined by the primers. Practical control of the sequential annealing, extension, and denaturation steps is exerted by varying the temperature of the reaction container, normally in a repeating cyclical manner. One of ordinary skill in the art would be aware of thermocycling machines which are available to automatically carry out the cycles of heating, cooling and heating. Annealing and extension occur optimally in the 400° C. to 80° C. temperature range (exact value depending on primer sequences, lengths, concentrations, salt concentrations, DMSO concentration, impurities in the reaction mixture), whereas denaturation requires temperatures in the 80° C. to 100° C. range (exact value depending on target sequence, target sequence length and concentration, salt concentration, DMSO concentration).

DNA amplification procedures by PCR are well known and are described in U.S. Pat. Nos. 4,683,195, 4,683,202, and 4,965,188, each of which is incorporated herein by reference. See PCR Protocols: A Guide to Methods and Applications [*PCR Protocols: A Guide to Methods and Applications.* (1990) Innis, M., Gelfand D., Sninsky, J; and White, T., eds., Academic Press, San Diego]. For ease of understanding the advantages provided by the present invention, a summary of PCR is provided. PCR requires two primers that are capable of hybridization with a single-strand of a double-stranded target nucleic acid sequence which is to be amplified. In PCR, this double-stranded target sequence is denatured and one primer is annealed to each single-strand of the denatured target. The primers anneal to the target nucleic acid at sites removed (downstream or upstream) from one another and in orientations such that the extension product of one primer, when separated from its complement, can hybridize to the extension product generated from the other primer and target strand. Once a given primer hybridizes to the target sequence, the primer is extended by the action of a DNA polymerase. DNA polyermase which is heat stable is generally utilized so that new polymerase need not be added after each denaturation step. Such thermostable DNA polyermase would be known to one of ordinary skill in the art such as Taq polymerase. The extension product is then denatured from the target sequence, and the process is repeated. One particular method for minimizing the effects of cross contamination of nucleic acid amplification is described in U.S. Pat. No. 5,035,996, which are incorporated herein by reference. U.S. Pat. No. 5,494,810 Barany, Francis, et al. "Polymerase chain reaction (PCR)" refers to a patented process (described in U.S. Pat. Nos. 4,683,202 and 4,683,195) for the exponential amplification of a specific DNA fragment by utilizing two oligonucleotide primers that hybridize to opposite strands and flank the region of interest in a target DNA are hereby incorporated by reference. Also, those assays disclosed in the disclosures of U.S. Pat. No. 4,459,359 is hereby incorporated by reference.

The present invention provides for the use of adaptamers to design, fashion or manipulate fragments for PCR/recombination-directed library construction. The present invention also provides for a method to connect non-contiguous fragments by using adaptamers for the construction of libraries by recombination.

In one embodiment the nucleic acid molecule is DNA, RNA or cDNA. In one embodiment, amplification is carried out using the polymerase chain reaction and a single or plurality of primer sets so as to provide PCR products of different lengths. In one embodiment, the plurality of primer sets are amplified together by PCR. In another embodiment, each primer-set is amplified separately by PCR. The pairs of primers may be about 20 base pairs apart or may be about 5 kilobases apart and the polymerase chain reaction is carried out with more time allotted to elongation in the PCR profile of times and temperatures programmed into the temperature cycler. The primers may be any distance apart as long as the distance is capable of being replicated during one PCR cycle. This technology is constantly changing and the ability of polymerases is also being refined. Thus, the present invention provides for the use of any polymerase capable of such activity as producing 5 kilobases or more, i.e. 10, 20, 30, 50, 100 kilobases. The present invention also provides for the primers of a pair to be about 100 bases apart, about 300 bases apart, about 800 bases apart, about 1200 bases apart or about 1600 bases apart.

As used herein, "library" encompasses at least two nucleic acid molecules representative of a particular set or group of nucleic acids. The set or group may be a genome of a particular species; a genome of an individual animal, human or cell; a group of mutations in a nucleic acid molecule; a cDNA group; a group of cDNAs representative of genes which are expressed in a cell in response to a certain drug or signal; a group of cDNA's representative of genes expressed in a cell during a particular stage of development or differentiation; a group of cDNAs of a cell specific to a disorder or of an individual which has a particular disorder or disease; a set of nucleic acids that code for a ligand of a particular receptor; a set of nucleic acids that code for receptors of a particular ligand; a set of nucleic acids representative of genes which are expressed in a particular cell type (skin libraries, ovarian libraries, neural libraries); a set of nucleic acids that are representative of the genes that are expressed in one cell type and not in another cell type (i.e., a subtraction library). There are many other kinds of libraries which would be known to one of ordinary skill in the art.

The library may be a set of plasmids in a bacterial cell, or a set of DNAs in separate specific tubes or a set of strains of cells, yeast or prokaryotic or eukaryotic, that have been manipulated via DNA transformation to create gene disruptions, fusions deletions and insertions. The library may be a set of nucleic acids harbored in a host cell, or in a replicable vector in a host cell. In addition, circular vectors that can be subsequently manipulated (e.g. auto-digested) can be created. See FIGS. 7 and 8.

The present invention provides for the construction of 2-hybrid libraries, expression libraries, fusion libraries, promoter capture libraries, insertion libraries, rearrangement libraries, libraries representative of a genome. The genome may be derived from a human, a mouse, a frog, an insect, a horse, a pig, a monkey, a fish, a fowl, a mold, a bacterium, a mitochondrium, an archeological artifact.

The present invention may be carried out with either the target nucleic acid or the foreign nucleic acid linked to a solid support. The present invention may utilize automated steps or robotics.

DNA primer pairs of known sequence positioned 10–4, 000 base pairs apart that are complementary to the plus and minus strands of the DNA to be amplified can be prepared by well known techniques for the synthesis of oligonucleotides. One end of each primer can be extended and may be modified to create restriction endonuclease sites when the primer is annealed to the target DNA. The PCR mixture may contain the target DNA, the DNA primer pairs, four deoxyribonucleoside triphosphates (A, T, C, G), $MgCl_2$, DNA polymerase (thermostable), and conventional buffers. The DNA can be amplified for a number of cycles (usually from 20–40 cycles). It is generally possible to increase the sensitivity of detection by using a multiplicity of cycles, each cycle consisting of a short period of denaturation of the target DNA at an elevated temperature, cooling of the reaction mixture, and polymerization with the DNA polymerase.

Choosing PCR primer sequences, preparing PCR reagents and reaction mixtures, and designing and running PCR are well known procedures in the PCR art. In the event that nucleic acid amplification is performed on suspended cells in a standard PCR test tube, the cells are treated like any conventional PCR test sample: diluted into reaction mixture shortly before amplification is started, at a total cell number ranging from approximately 100 to approximately $10_6$. Enzyme, primers, target nucleic acid, dNTPs, $MgCl_2$ and buffer is mixed into a reaction mixture. After 50 to 100 µl of mineral oil have been added to the reaction tube, the tube is placed in a thermal cycler, many versions of which are commercially available from suppliers such as Perkin Elmer Cetus Instruments, and heated to a temperature between about 50° C. and about 80° C., preferably between 70° C. and 80° C.

If multiple samples are amplified simultaneously in different tubes, a fresh sampler tip is used to add the missing reagent(s) to each tube, to prevent cross-contamination. After all tubes have been prepared and capped, the standard three-temperature thermal cycle program of denaturation, annealing, and extension for approximately 10 to 40 cycles is performed under thermal cycler microprocessor control. Alternatively, and often preferably, a series of two-temperature cycles can be run wherein annealing and extension are performed at a single temperature, normally optimized for stringent annealing of primer to template. Because reaction rates may be somewhat retarded with cellular preparations as compared to cell-free nucleic acids, it may be necessary to increase the durations of the denaturation, anneal, extend, or anneal-extend cycle segments as much as several-fold from values standard when the test sample contains cell-free nucleic acid. This adjustment easily is performed by trial and error, looking for conditions which maximize the intensity of the signal seen during amplified nucleic acid detection or which minimize the number of cycles needed to reach a given signal intensity. A similar optimization procedure can be used for $MgCl_2$, dNTP, primer, and enzyme concentrations in the reaction mixture; these parameters often show different optima for different targets, and also may be affected when amplification occurs within fixed cells.

Primer pairs of known sequence positioned 10–300 base pairs apart that are complementary to the plus and minus strands of the DNA to be amplified can be prepared by well known techniques for the synthesis of oligonucleotides. Synthetic olionucleotides are well known to one of ordinary skill in the art and are available from companies such as Oligos, Etc.

Oligonucleotides for use as probes or PCR primers may be chemically synthesized according to the solid phase phosphoramidite triester method first described by Beaucage and Carruthers [Beaucage and Carruthers (1981) *Tetrahedron Lett.* 22:1859–1862]using an automated synthesizer, as described in Needham-VanDevanter [Needham-VanDevanter, D. R., et al., (1984) *Nucelic Acids Res.* 12:6159–6168]. Purification of oligonucleotides is by either native acrylamide gel electrophoresis or by anion exchange HPLC as described in Pearson, J. D. and Regnier, F. E. [Pearson, J. D., and Regnier, F. E., (1983) *J. Chrom.* 255:137–14976.]. The sequence of the synthetic oligonucleotide can be verified using the chemical degradation method of Maxam, A. M. and Gilbert, W. [Maxam, A. M. and Gilbert, W. *Methods in Enzymology* (1980) Grossman, L. and Moldave, D., eds., Academic Press, New York, 65:499–560.].

The present invention also provides for computer programs that carry out the choice of primers for each particular target and foreign nucleic acid. Such computer program would utilize known nucleic acid sequences such as Genbank sequences or ATCC sequences in order to evaluate and choose the best primers for a particular purpose. The program would take into account the ultimate purpose or use of the primers or adaptamers and the region of interest of the target nucleic acid and the sequence and region of interest of the foreign nucleic acid. This computer program would be useful in designing adaptamers for the production of specific libraries and for the production of nucleic acids. The computer program would also be useful for antisense design and fusion protein design and gene therapy design.

As used herein, "amplification" is a special case of nucleic acid replication involving template specificity. It may be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be amplified or detected preferentially in the presence of other non-target nucleic acid sequences. Amplification techniques have been designed primarily for the detection of specific target sequences. Template specificity is achieved, in most amplification techniques, by the choice of enzyme. Amplification enzymes are enzymes that, under the conditions in which they are used, will process only specific sequences of nucleic acid in a heterogenous mixture of nucleic acid. For example, in the case of Q beta replicase, MDV-1 RNA is the specific template for the replicase. (See D. L. Kacian et al., Proc. Natl. Acad. Sci. USA 69:3038 (1972) at p.853 Abstract.) Other nucleic acids will not be replicated by this amplification enzyme. Similarly, in the case of T7 RNA polymerase, this amplification enzyme has a stringent specificity for its own promoters. (See M. Chamberlin et al., Nature 228:227 (1970) at p.229, col 2.)

In the case of T4 DNA ligase, the T4 ligase will not ligate the two oligonucleotides where there is a mismatch between the oligonucleotide substrate and the template at the ligation junction. (See D. Y. Wu and R. B. Wallace, Genomics 4:560 (1989).) Finally, Taq polymerase, by virtue of its ability to function at high temperature, is found to display high specificity for the sequences bounded and thus defined by the primers; the high temperature results in thermodynamic conditions that favor primer hybridization with the specific target sequences and not hybridization with non-target sequences. (See R. K. Saiki in PCR Technology, Principles and Applications for DNA Amplification (H. A. Erlich, Ed.), pp. 7–16 (1989).)

Some amplification techniques take the approach of amplifying and then detecting target; others detect target and then amplify probe. Regardless of the approach, the sample containing nucleic acid must be free of inhibitors for amplification to occur at high efficiency.

Amplification "reagents" are defined as those reagents (primers, salt, buffers, lables, deoxyribonucleotide triphosphates, etc.) needed for amplification except for nucleic acid and the amplification enzyme. Typically, amplification reagents along with other reaction components are placed and contained in a reaction vessel (test tube, microwell plate, microfuge tube, etc.). Synthetic oligonucleotide primers are available commercially. See Perkin-Elmer Cetus Biotechnology Catalog, Oligos, Etc. and other companies.

If a biological sample is the source of nucleic acid, one may disrupt the cellular integrity of the biological sample by applying a lysate to the sample. One lysing agent is protease K. Protease K is a proteolytic enzyme from *Tritirachium album*. It is particularly useful in the present invention because it has no significant DNase activity and, therefore, does not degrade nucleic acid which would prevent amplification. It is also attractive because it is inexpensive and commercially available (e.g., Sigma, St. Louis, Mo., U.S.A., catalogue No. p4914 "Proteinase K"). Various treatment conditions using protease K have been found useful. It is preferred that a high concentration of protease K (e.g., 1.5–2.5 mg/ml) be used for short (5–10 minutes) incubation periods to completely degrade cellular and viral protein and expose viral nucleic acid for amplification. When lower concentrations of protease K (e.g., 0.5 mg/ml) are used, longer incubation periods (30–60 minutes) are required to achieve the same effect. Other lysis approaches are also contemplated, including lysis by heating.

The present invention also contemplates labeling methods wherein the oligonucleotide primer sequences have at least one label attached or integrated into its structure. One embodiment of the present invention is an adaptamer with a label attached at the 5' end. Labels are generally intended to facilitate the detection of the nucleic acid in subsequent steps. Labels are chosen from the group consisting of enzymes, fluorophores, high-affinity conjugates, chemiphores and radioactive atoms ("radiolabels"). While other labels may be used, the present invention contemplates: 1) the enzymes alkaline phosphatase, beta-galactosidase and glucose oxidase; 2) the affinity conjugate system of biotin-avidin; 3) the fluorophore that is fluorescein; 4) the chemiphore that is luminol; and 5) the preferred radiolabels $^3$H, $^{14}$C and $^{32}$P. Oligonucleotides may be 3' end-labeled with [$\alpha$-$^{35}$S] dATP to specific activities in the range of $1\times10^{10}$ dpm/$\mu$g using terminal deoxynucleotidyl transferase. Unincorporated labeled nucleotides can be removed from the nucleotide probe by centrifugation through a Sephadex G-25 column or by elution from a Waters Sep Pak C-18 column. Where the nucleic acid (primer, adaptamer, target, foreign, first-fourth) is labeled, the labels can include radioisotopes, fluorophores, enzymes, luminescers or particles. These and other labels are well known in the art and are described, for example, in the following U.S. Pat. Nos. 3,766,162; 3,791,932; 3,817,837; 3,996,345; and 4,233,402.

"Detection" of PCR-amplified nucleic acid refers to the process of observing, locating, or quantitating an analytical signal which is inferred to be specifically associated with the product of PCR amplification, as distinguished from PCR reactants. The analytical signal can result from visible or ultraviolet absorbance or fluorescence, chemiluminescence, or the photographic or autoradiographic image of absorbance, fluorescence, chemiluminescence, or ionizing radiation. Detection of in situ PCR products involves microscopic observation or recording of such signals. The signal derives directly or indirectly from a molecular "tag" attached to a PCR primer or dNTP or to a nucleic acid probe, which tag may be a radioactive atom, a chromophore, a fluorophore, a chemiluminescent reagent, an enzyme capable of generating a colored, fluorescent, or chemiluminescent product, or a binding moiety capable of reaction with another molecule or particle which directly carries or catalytically generates the analytical signal. Common binding moieties are biotin, which binds tightly to streptavidin or avidin, digoxigenin, which binds tightly to anti-digoxigenin antibodies, and fluorescein, which binds tightly to anti-fluorescein antibodies. The avidin, streptavidin, and antibodies are easily attached to chromophores, fluorophores, radioactive atoms, and enzymes capable of generating colored, fluorescent, or chemiluminescent signals.

For this purpose, nucleic acid molecules generated by the present invention or their subsequent expression products can be radioactively labeled metabolically in vivo by culturing cells expressing the nucleic acids generated in the presence of $^{35}$S-cysteine and $^{35}$S-methionine (200 Ci/ml) in RPMI 1640 medium devoid of these two amino acids and supplemented with dialyzed fetal calf serum. After 16 hours, the labeled protein may be harvested from the culture supernatant by centrifugation over a 20% sucrose cushion at 100,000 g for 1,5 hours if such-protein is secreted from the cell. Otherwise, the cells may be collected and the protein purified. The resulting pelleted protein is then resuspended in RIPA buffer (20 mM triethanolamine, pH 8.0, 0.5 M NaCl, 0.5% Nonidet P40, 0.1% sodium deoxycholate, and 1 mM phenylmethylsulfonylfluoride).

"Nucleic acid probe" refers to an oligonucleotide or polynucleotide containing a sequence complementary to part or all of the PCR target sequence, also containing a tag which can be used to locate cells in an in situ PCR preparation which retains the tag after mixing with nucleic acid probe under solvent and temperature conditions which promote probe annealing to specifically amplified nucleic acid.

A probe generated in such a manner can be employed in a diagnostic test for specific detection of a particular nucleic acid which incorporates the following essential steps: (1) labeling of the probe generated as described above by the methods previously described; (2) bringing the probe into contact under stringent hybridization conditions with DNA from, once said DNA or RNA has been, preferably, applied to a membrane and has been rendered accessible to the probe, (3) washing the membrane with a buffer under circumstances in which stringent conditions are maintained, detection of the labeled probe, preferably by autoradiography in cases in which the probe has been radioactively labeled, or by a suitable immunodetection technique in case the probe has been labeled chemically.

RNA is prepared by any number of methods; the choice may depend on the source of the sample and availability. Methods for preparing RNA are described in Davis et al., 1986, Basic Methods in Molecular Biology, Elsevier, NY, Chapter 11; Ausubel et al., 1987, Current Protocols in Molecular Biology, Chapter 4, John Wiley and Sons, NY; Kawasaki and Wang, 1989, PCR Technology, ed. Erlich, Stockton Press NY; Kawasaki, 1990, PCR Protocols: A Guide to Methods and Applications, Innis et al. eds. Academic Press, San Diego; and Wang and Mark, 1990, PCR Protocols: A Guide to Methods and Applications, Innis et al. eds. Academic Press, San Diego; all of which are incorporated herein by reference.

As used herein, "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, Ausubel, F., et al., Methods in Enzymology [*Methods in Enzymology* Vol. 152, (1987) Berger, S. and Kimmel, A. ed., Academic Press, New York] or Hybridization with Nucleic Acid Probes all of which hereby are incorporated herein by reference.

High stringent hybridization conditions may be selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For example high stringency may be attained for example by overnight hybridization at about 68° C. in a 6×SSC solution, washing at room temperature with 6×SSC solution, followed by washing at about 68° C. in a 6×SSC in a 0.6×SSX solution.

Hybridization with moderate stringency may be attained for example by: 1) filter pre-hybridizing and hybridizing with a solution of 3×sodium chloride, sodium citrate (SSC), 50% formamide, 0.1M Tris buffer at Ph 7.5, 5×Denhardt's solution; 2.) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4×for 1 minute each at room temperature at 4×at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectivly hybridizing it is meant that a probe binds to a given target in a manner that is detectable in a different manner from non-target sequence under high stringency conditions of hybridization. in a different "Complementary" or "target" nucleic acid sequences refer to those nucleic acid sequences which selectively hybridize to a nucleic acid probe. Proper annealing conditions depend, for example, upon a probe's length,base composition, and the number of mismatches and their position on the probe, and must often be determined empirically. For discussions of nucleic acid probe design and annealing conditions, see, for example, Sambrook et al., [Sambrook, et al. (1989) *Molecular Cloning: A Laboratory Manual* (2nd ed.), Cold Spring Harbor Laboratory, Vols. 1–3.] or Ausubel, F., et al., [Ausubel, F., et al. (1987) *Current Protocols in Molecular Biology*, New York.].

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, or by the triester method according to Matteucci, et al., [Matteucci, et al. (1981) *Am. Chem. Soc.* 103:3185.], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

One advantage of the present invention is that it allows one to bypass the requirement of an intermediate host (e.g. *E. coli* and eliminates the need for ligation in library construction. Another advantage of the present invention is that it permits a "prethought" orientation to be constructed by simple altering of the adaptamer "junction" fragment. Whichever sequences are chosen for the 5' and 3' regions of the adaptamers will then dictate the final configuration of the fragment arrangement.

Figure 2:
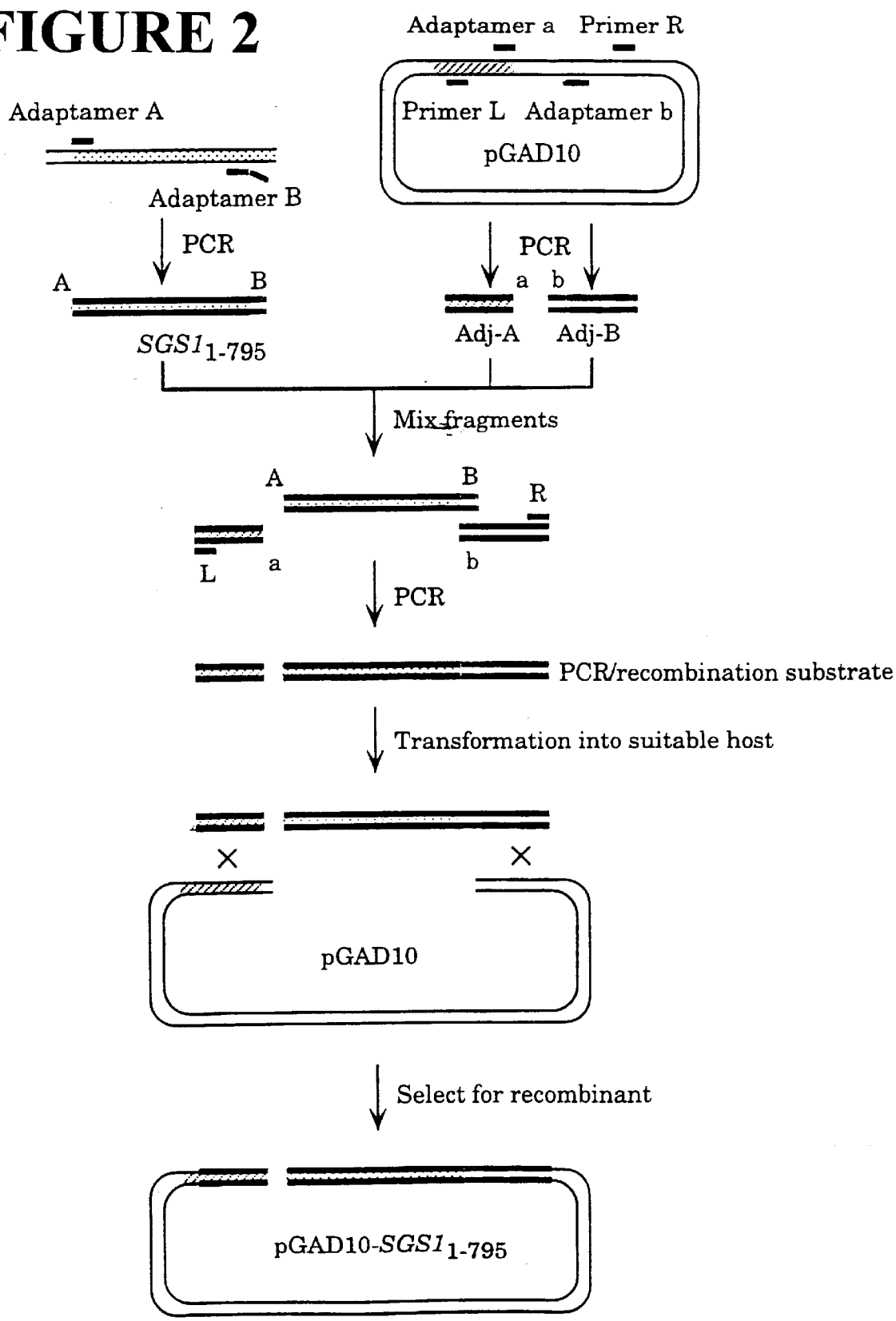
FIG. 2. Schematic diagram of the experiment to demonstrate the feasibility of PCR/recombination-directed library construction.

As to FIG. 2, the choice of the fourth molecule, which sequences are amplified from it and which sequences are linked to it in the adaptamer determines what the fusion will be. In the region that is homologous on either molecule [(labeled Adj-A in FIG. 2) or (labelled Adj-B in FIG. 2)], the adaptamer is designed so that the amplified molecule (labeled SGS1 $_{1-795}$ in FIG. 2) fuses in a prearranged, preplanned fashion with the adjacent fragments. This will be the end product of the second round of PCR.

The present invention provides for adaptamers (an adapted type of primers) that use the common sequences that flank every member of the library. One or both of the adaptamers may contain additional designed nucleotides (1 nucleotide, 2 nucleotides—or n nucleotides) inserted between the complementarity of the adaptamer used on the EST molecule. (See FIG. 6). A specific example may be using 0, 1 and 2 would produce one in three in-frame fusions from randomly ended (i.e. in the middle of coding sequence) ORF (open reading frame) sequences. When n is larger, any pre-arranged sequence that can be synthesized via synthetic oligonucleotide chemistry can be inserted at a precise point for all of the members of a library. These extra nucleotides could be DNA binding sites or tags or they could encode "extra" amino acids that might give flexability to the novel joint created between the sequences or the extra nucleotides might give rise to or provide an antigen or other kind of protein tag.

The present invention provides for a method like claim 1 wherein the 3' end of the primer described in 1 (A)(i)(a) is homologous to a common replicative element (e.g. Alu sequence, LINE, B1, etc.). In this case, the orientation of the other primer must be toward the 5' direction of the ORF. This permits promoter capture.

Linking two fragments is the minimum for adapting any random sequence by PCR/recombination-directed library construction. See FIGS. 12, 13 and 14A–F. Any number of fragments may be linked together. All that is required is that the adaptamers at each end are unique and will not overlap any other adaptamer (except the correct complementary one) or amplify any internal sequences (because this could cause incorrect joints or connections between fragments to be formed). This permits the fusion of novel sequences adjacent to any other fragment.

Figure 16:
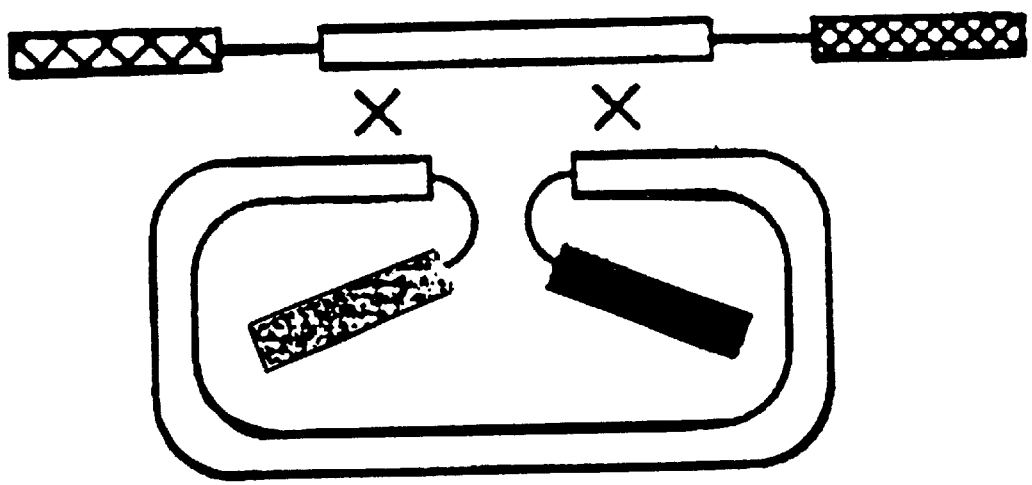
FIG. 16. Two nucleic acid molecules capable of cross-over recombination with four different counter-selectable markers on each end of each nucleic acid molecule. Thus, one is capable of selecting against these four markers and thus selecting for a more rare, correct cross-over event.

The present invention also provides for circular molecules. A circular molecule may be formed in some organisms (such as mammalian cells) if one can counterselect a genetic marker that is placed on the ends of the preliminary linear molecule (the starting material). Such a scheme would require an additional fragment to be added to the ends of each circular molecule which could be done by using adaptamers as described herein. FIG. 16 shows the configuration of this recombination event in an extreme version all four ends have counterselectable markers.

In the practice of the present invention, specific sequence requirements of each particular use must be known in order to prevent adaptamers from priming non-productive products, that is products which would not work as starting material for the next step of the method. The sequences chosen for amplifying two different fragments from the second molecule must be very carefully defined. FIG. 14A illustrates an insertion and FIG. 14B illustrates an insertion accompanied by a deletion if Adaptamer b and Adaptamer A are separated thus having some distance of sequence between them. FIG. 14C depicts an insertion accompanied by a duplication which may be obtained if the sequences projected for amplification from each pair of primers (Primer L/Adaptamer A and Adaptamer b/Primer R) cross one another upon amplification. The figure shows what will happen after the PCR/recombination fragment is synthesized and is introduced back into the parental molecule (ii) which was used to generate the flanking sequences that allowed recombination.

The configuration shown in FIG. 14D is also important in that it can be used to "gap repair" a genomic sequence that lies between the position of adaptamers (c) and (f). This is not directly related to library construction, but it is a useful kind of manipulation that is possible with adaptamers. Similarly, the FIG. 14E configuration may be used for directed gene replacement on a per gene basis and is not useful for library construction. It is useful in the following situations: A mutation from one strain of yeast can be transferred into another strain of yeast by designing the c, d, e, and f adaptamers as shown in FIG. 14C making sure that the mutation of interest is in the shaded (and thus duplicated) region. As this PCR/recombination fragment is introduced into the genome of interest (one without the mutation), recombination removed the non-mutated region and replaces it with an insertion flanked by a duplicated copy of the mutated region. A second recombination event, this time direct repeat recombination, can be selected resulting in the loss of the intervening insertion and leaving a single copy of the mutated sequence in the genome. A variation of this method has been carried out in yeast and would probably work in mammalian cells as well. This invention provides for genetic manipulation of genomes using PCR/recombination-directed methods.

The present invention provides a method for the use of adaptamers to create two separate molecules for recombination into the genome such that the host organism resolves them into the correct configuration. The present invention provides for a combination of fusion of two nucleic acids and the reiteration of such method of generating a fused nucleic acid molecule so as to fuse two or more nucleic acid molecules. FIG. 14D shows the pairing required for this integration. In this embodiment, the adaptamers for the two fragments are designed to yield an overlap for the selectable marker such that only recombination in the appropriate alignment will result in a functional gene. The present invention provides for the addition of "blocking" counter-selectable markers at the two ends that pair with the target DNA.

This invention is illustrated in the Experimental Details section which follows. These sections are set forth to aid in an understanding of the invention but are not intended to, and should not be construed to, limit in any way the invention as set forth in the claims which follow thereafter.

Experimental Details

EXAMPLE 1

One embodiment of the subject invention is to optimize the steps necessary to utilize a newly developed technique called PCR/recombination-directed library construction to facilitate genome-wide analysis. The method may utilize the "EST"sequences deposited in dbEST. At least four separate embodiments may be enumerated:

(i) Optimization of the use of unique primers called "adaptamers" (see FIGS. 1 and 2) to construct libraries directly in yeast avoiding completely the need to use bacteria as an intermediary.

(ii) Augmentmentation of high frequency transformation methods so that they can be scaled up for the efficient introduction of these libraries into the appropriate host cells.

(iii) Design of adaptamers to permit the amplification of random EST clones and their in-frame fusion with DNA binding domains and transcriptional activation domains for use in the two-hybrid system.

(iv) Optimization of the construction of two-hybrid fusion proteins using adaptamers and mRNA (cDNA) as the template to obviate the necessity of having a full length clone in hand to make a fusion for two-hybrid analysis.

The methods outlined here are not specific for mammalian sequences and can be applied to any sequenced genome. For example, a two-hybrid library for any sequenced genome (e.g., bacteria) can be constructed in yeast using adaptamers.

The availability of the complete genomic sequences for several organisms as well as extensive EST databases for several others provides a challenge and an opportunity to exploit this information creatively to help determine the function of these genes. By applying genome-wide experimental approaches, one can both facilitate and further the study of biology in these systems with great power. For example, construction of an arrayed library of genes/ESTs for use in a two-hybrid analysis is a logical next step for the characterization of these open reading frames. One approach to constructing such libraries involves the creation of random libraries, first by cloning cDNAs into vectors, tranforming bacteria and then transferring the clones into yeast. The experiments are performed such that only information about positive interactions can be derived. Given that there is now considerable data being collected for many potential ORFs, such as ESTs or ORFs from complete genomic sequences, a more direct method of library construction is possible that bypasses the need to create random clone libraries. Instead, clones can be made from the sequence information by creating a PCR-generated fragment that is designed to contain overlapping sequence with the target vector. Co-transformation of this PCR fragment and the linearized vector directly into yeast selects for efficient in vivo recombinants. In addition, as the primers are designed from known sequences, in the cases where sequences at the 5' and 3' ends of an open reading frame are known, the clone can be generated directly from mRNA without the need for a full length cDNA clone.

Methods to simplify the construction of an arrayed library may be carried out by combining PCR methods and the power of homologous genetic recombination ("PCR/recombination-directed library construction"). The system described is an "open" system: once created, any type of gene fusion can be made in a completely specific, arrayed, genome-wide library.

The development of these libraries and demonstration of the feasibility of this approach may provide the basis for the construction of genome-wide libraries. The distribution of such libraries within the research community will provide powerful and flexible tools for all biologists who will be exploring the function of genes. These approaches may also provide a paradigm for studies in other systems that may take place in the future.

Preliminary Studies

There are established methods and methods in development regarding the manipulation of yeast. These include gene targeting [1] and gene disruptions methods [2] that utilize genetic recombination for genome alterations.

Several yeast strains have been developed to produce a mating method for streamlining two-hybrid analysis [3]. Recently, a cycloheximide resistance marker, cyh2, has been introduced into these strains to permit the rapid counter-selection of a plasmid bearing a CYH2 wild type gene. The strains already have can1 mutations to permit the counter-selection of a plasmid-borne CAN1 gene. The combination of these counterselectable markers into two-hybrid plasmids is used to help screen out false positives.

There exists experience with PCR methodology of one of skill in the art to include the design and successful implementation of 376 STSs for human chromosome 13 [4]. PCR has been used to generate long fragments of the mouse Rad52 genomic sequence to determine the primary sequence of more than 21 kb of this gene. 2 to 3 kb PCR products are routinely generated which can be directly used on an ABI sequencer.

It has been established that yeast cells will efficiently recombine overlapping fragments to create circular molecules. As few as 20 nucleotides of homology can be used as the recombination substrates however, the efficiency is low and there is the possibility that aberrant events can be generated [5, 6]. To obviate the necessity to synthesize longer oligomers to increase the efficiency of the recombination event, an approach has been designed that extends the overlapping homology using PCR in a generic fashion so that only a single set of unique primers need to be constructed for each fragment of interest. These primers have been termed adapted primers or "adaptamers".

To demonstrate the feasibility of the adaptamer approach to create clones, the following experiment was performed. As shown in FIG. 1, an adaptamer is a PCR primer that contains additional DNA sequence on its 5' end (a tag, an adapted region) to permit fusion to any adjacent sequence containing the complementary sequence to the tag. For open reading frames, the convention was adopted that the 5' end adaptamer is called A and the 3' end adaptamer, B. A lower case letter (a or b) is used to indicate a complementary adaptamer. The fragments used as recombination substrates are named Adjacent-A (Adj-A) and Adjacent-B (Adj-B) and are made from adaptamer a and primer L and adaptamer b and primer R (see FIG. 2 for orientations) that are homologous to the target vector. The length of Adj-A and Adj-B determine the amount of overlap with the target vector.

In the test experiments of this strategy, two 36 nucleotide long adaptamers were designed. Adaptamer A contains 18 nucleotides of homology at the AUG start codon of the SGS1 open reading frame [7] and adaptamer B, 18 nucleotides of homology ending at codon 795. The 18 nucleotides comprising the A and B tag sequences overlap with the, insertion site on the pGAD10 vector used for two-hybrid analysis [8]. Adaptamer a and primer L generate a 255 bp product on one side of the cloning site of pGAD10 while adaptamer b and primer R generate a 250 bp fragment from the other side of the cloning site. The A/a and B/b sequences were designed so that the 795 aa ORF of Sgs1 would be fused in frame with the activation domain of pGAD10. This creates a fusion protein that can interact with Top3, which has been fused to the Gal4 DNA binding domain. These constructs were used so that one could validate the in vitro PCR and recombination reactions since successful clones will turn blue when yeast transformants are mated to the Top3 fusion strain. In addition, the adaptamers were designed so that the untemplated A often added by the Taq polymerase would not disturb subsequent pairing and priming reactions.

Figure 3:
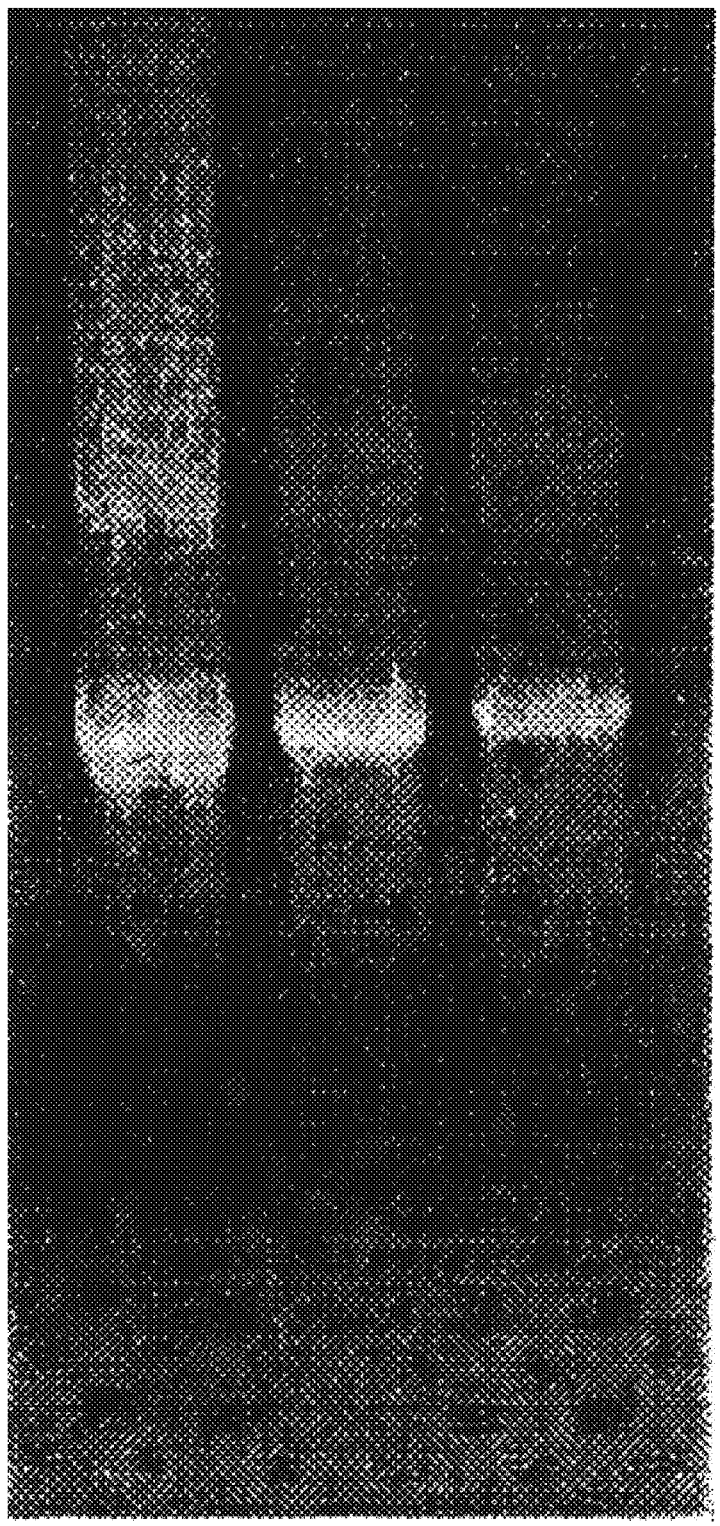
FIG. 3. Ethidium bromide stained gel electrophoresis of three-reactions used to create the PCR/recombination substrate described in FIG. 2. Lane 1 shows the product of a reaction where the three fragments (Adj-A, $SGS_{1-795}$, and Adj-B) were mixed in a 1:1:1 ratio prior to gel purification. Lanes 2 and 3 show the products obtained using purified fragments mixed in a 1:2:1 and a 1:4:1 ratio, respectively.

Two experiments were performed with these primers. First, the three PCR products were generated using 30 cycles at standard PCR conditions (94° C., 30"; 55° C., 15"; 73° C., 30") and gel purified. They were mixed in two different ratios (Adj-A:Sgs1:Adj-B): 1:2:1 and 1:4:1 and excess primers L and R (1 μM) were added and "long" PCR was performed (94° C., 10"; 55° C., 30"; 72° C., 4' for 10 cycles then 20 cycles where the 72° C. step is ramped by extending each cycle 30 additional seconds). Both gave the same result which is illustrated in FIG. 3 as a clean, 2.8 kb fragment (FIG. 3, lanes 2 & 3). At the same time, the three fragments were mixed at equimolar concentrations prior to gel purification of the PCR products and similar results were obtained (FIG. 3, lane 1). The products of these PCR reactions were used directly in a co-transformation experiment with linearized pGAD10 that was digested with XhoI and EcoRI to help reduce background religation events of the vector.

Yeast transformation by both electroporation and lithium acetate methods was performed. For electroporation, co-transformation with 100 ng of vector and 100 ng of the PCR/recombination substrate resulted in 564 transformants, 15 times more than the 35 observed with vector alone. For lithium, it was found that more than 8,000 transformants occurred when the two fragments were co-transformed as compared to 200 for the vector alone. A sample of the transformants were tested for fidelity by measuring their ability to form blue colonies after mating with a strain bearing the TOP3-GDB fusion. 95% of the colonies turned blue.

Figure 4:
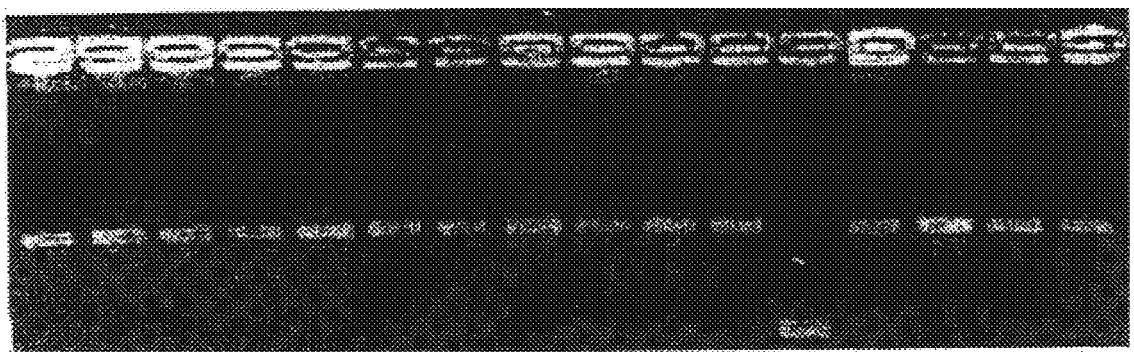
FIG. 4. Sixteen transformants were analyzed by colony PCR using primers L and R to determine the insert size. The smaller band indicates a single example that does not contain an insert.

In addition, FIG. 4 shows 15 out of 16 transformants from a similar experiment exhibit the correct recombination joints. These results indicate that PCR/recombination-directed library construction would work and is a feasible method.

It was also demonstrated that mRNA may be used directly in a PCR/recombination-directed cloning experiment. The use of mRNA directly, obviates the need to have a full-length copy of the cloned gene of interest. Additionally, any fragment of a gene can be cloned into a vector of choice just by choosing the appropriate sequences for the adaptamers. In the test described herein, adaptamers were made to the mouse RAD52 gene starting at amino acid 56 and ending 370 bases from the termination codon (a 1366 nucleotide long fragment). 20 μg of total mouse RNA from 7.5 day mouse embryonic liver was converted to DNA; in a 33.5 μl reaction using 2.5 μM oligo d(T)$_{16}$ (Perkin-Elmer, Cat. No. N808-128) as a primer. The reaction was heated to 65° C. for 15 minutes and 60 units of mRNazin (Promega, Cat. No. N251A), 1 nM each of dATP, dCTP, dGTP and dTTP. 0.1 μg/ml final BSA and 100 units of M-MuLV reverse transcriptase (NE BioLabs, Cat. No. 253L) were added in RT buffer (NE BioLabs). After 1 hr at 37° C., the 50 μl reaction was extracted twice with phenol:chloroform, ethanol precipitated and resuspended in 50 μl of H$_2$O. 3 μl of the cDNA was used for two "long" PCRs (94° C., 10"; 55° C., 30"; 72° C., 4' for 10 cycles then 20 cycles where the 72° C. step is ramped by extending each cycle 30 additional seconds). The reaction products were gel purified (≈10 ng total) and resuspended in 20 μl. 1 μl of this was used for a second round of "long" PCR and again gel purified. Adj-A and Adj-B (described above) were mixed in three different molar ratios (Adj-A:Rad52:Adj-B): 15:1:29; 2:1:4 and 3:1:2 and excess primers L and R (1 μM) were added. In addition to the expected 1.9 kb fragment, the 15:1:29 ratio gave a smaller and more intense band. This reaction was not used for further experiments. The 2:1:4 and 3:1:2 ratio reactions each gave the expected 1.9 kb fragment. These fragments were gel purified and used in a co-transformation experiment with linearized XhoI-EcoRI-digested pGAD10. Table 1 below shows the results.

| Ratio | PCR/recombination fragment | pGAD10 vector | Number of transformants | Number of insert positive clones |
|---|---|---|---|---|
| 2:1:4 | 0 | 12 ng | 160 | not applicable |
|  | 1.25 ng | 12 ng | 2,040 | 5/55 |
|  | 5 ng | 12 ng | 4,540 |  |
| 3:1:2 | 0 | 12 ng | 39 | not applicable |
|  | 18 ng* | 12 ng | 1056 | 1/22 |
|  | 12 ng | 12 ng | 156 | 12/18 |

*this sample was not gel purified before transformation

Figure 17A:
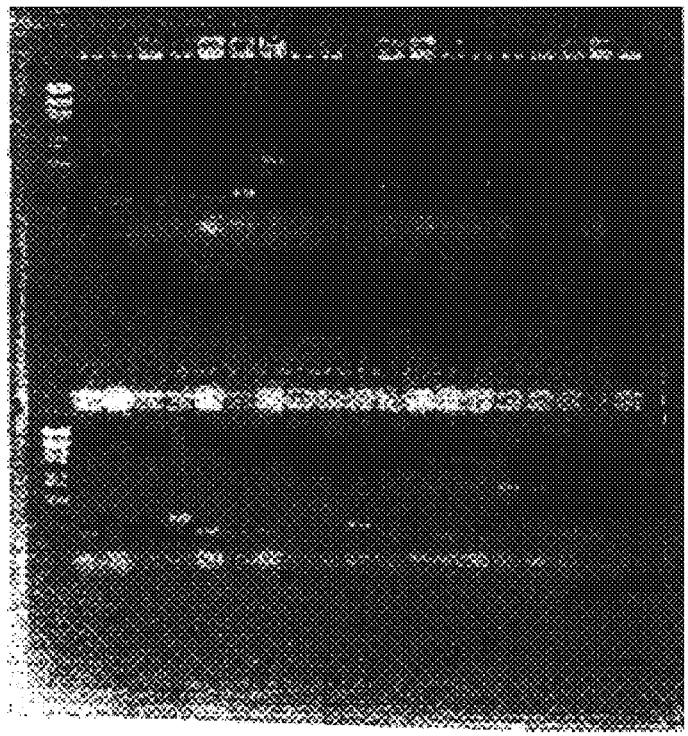
FIGS. 17A and 17B. Ethidium bromide stained products separated via gel electrophoresis. The bands shown are products derived from the methods described herein wherein the foreign nucleic acid and the target nucleic acid were derived from an mRNA or a cDNA.
Figure 17B:

Among the insert positive clones, some clones were found that were approximately 100 nucleotides shorter that the expected 10 size shown in FIGS. 17A–17B (compare lanes 4 and 5 of FIG. 17B). DNA sequence analysis of one of those clones revealed that it arose from a PCR product representing alternatively spliced mRNA similar to what has been observed that such sized fragments are produced from cloned cDNAs.

Research Design and Methods: Optimization of PCR/recombination-directed Library Construction As described in the hereinabove in the preliminary results section, it has been demonstrated that PCR/recombination-directed library construction is a viable approach for making clones. However, the optimization of several steps are necessary before this method can be applied to genomic scale. The length of the adjacent fragments in the first experiments were approximately 250 nucleotides. At this length, over 95% of the recombinant clones were correct. Optimization of this length is important. since the shorter these sequences are, the less they contribute to the overall length of the PCR product that recombines with the vector. At the same time, it is essential not to shorten these sequences too much as to reduce the efficiency of recombination in yeast. For all of the experiments described in this section, the same SGS1$_{1-795}$ fragment described earlier will be used which allows a biological as well as a physical assay for successful constructs (see Preliminary Studies). To optimize the length, the size of Adj-A and Adj-B will be varied from 40 to 500 nucleotides. One may plot not only the efficiency of transformation vs. length but also the percentage correct configurations vs. length. It is expected that 150 to 250 nucleotides will be optimal. However, it may be that 40 or 50 nucleotides are as efficient, thus one could eliminate the second round of PCR necessary to add the extra nucleotides of the adjacent sequences. From the results described herein, it is unlikely that 40 or 50 nucleotides will be optimal.

To optimize the conditions for adding Adj-A and Adj-B, the amount of each product added will be varied, along with the concentration of primers L and R. There are at least two possible scenarios for the addition of these adjacent fragments. In the initial experiments, small amounts of Adj-A and Adj-B and excess primers L and R were added (see Preliminary Studies). It may be possible to eliminate the addition of primers L and R by adding excess Adj-A and Adj-B. These can easily be synthesized as they are always the same for each vector being used.

These manipulations may eventually be performed by a robotics system, thus it is advantageous to remove as many steps as possible and to tailor reaction volumes accordingly. For example, the first PCR reaction to create the gene of interest using adaptamers A and B wall be done in the absence of the Adjacent-A and Adjacent-B adaptamers. A small portion (1/100th) will be removed and reacted with the Adj-A and Adj-B fragments to generate the optimally long recombination fragment for co-transformation into yeast with the vector of choice. However, it may be possible to add all of the components to the initial tube and let the PCR generate, in one reaction, the recombination fragment.

(2) Augmentation of High Frequency Transformation Methods

Besides optimizing the generation of recombination fragments, optimal transformation methods must be developed so that the library is minimally manipulated. Since the two-hybrid system is scored positively only if an interaction takes place, and the clones are made by mating, it is not necessary to have a 100% pure colony to assay. For example, as long as some proportion of the colony contains cells with the appropriate construct, a positive signal will be scored. Therefore, the transformation method must be efficient and easy to scale. It is clear that the $Li^+$ ion method [Ito, et al. J. Bacteriol. 1983, 153:163–68 and Gietz et al. 1992, Nucl. Acids Res. 20:1425] is the easiest to scale. Protocols for 96-well micotitre dish transformations have been developed and are well known to one of skill in the art. One could transpose the volumes and procedures of these methods with respect to the volumes of the PCR used to create the recombination fragment and the vector in order to generate some number of transformants per well. This number can be determined experimentally (30–50 is one possible approximation). Thus, even if cloning artifacts occur during PCR/recombination library construction either by accident or by design (see the next section for the "by design" example), some number of transformants will be correct. Experimentally, one may vary the proportion of positive clones in a colony to determine the percentage required to be correct and still give rise to a positive signal.

The present invention provides for a method that will allow yeast transformtion to take place entirely within the well of a microtiter dish. For such a protocol to be successful, one must ensure high enough efficiency transformation as well as efficient transfer of the mixed transformants to subsequent steps of the procedure. In addition, the optimization of transformation will take into account the volumes generated by PCR to create. This will be critical for the robotization of the process. However, even if larger volumes are necessary than can easily be accommodated in a microtiter well, one can still miniaturize the process to do multiple transformations at once. Such approaches avoid the purification of the clones which is a time consuming step. In addition, as discussed above, there is a distinct advantage to not purifying clones since positives will arise even if they are only a fraction of the colony.

(3) Design and Optimization of Random EST Cloning

The adaptamer approach outlined in the introduction can be used to make a clone for any known set of sequences by individually synthesizing a specific set of adaptamers. The use of this approach for the creation of fusions directly from known mRNA sequences will be described in the next section. However, the approach can also be used to create a library from EST sequences that have already been cloned. For example, I.M.A.G.E. has provided Washington University in St. Louis with many EST libraries. Many of these clones have been sequenced and they comprise dbEST. Sequences from these ESTs can be inserted directly into two-hybrid fusion vectors using the strategy described below. Two assumptions for this strategy are: (1) the 5' ends of the EST clones are often in the coding sequence of the EST, which will permit a productive fusion and (2) most clones do not exceed 5 kb in length as such sequences are not efficiently amplified by PCR.

Figure 6:
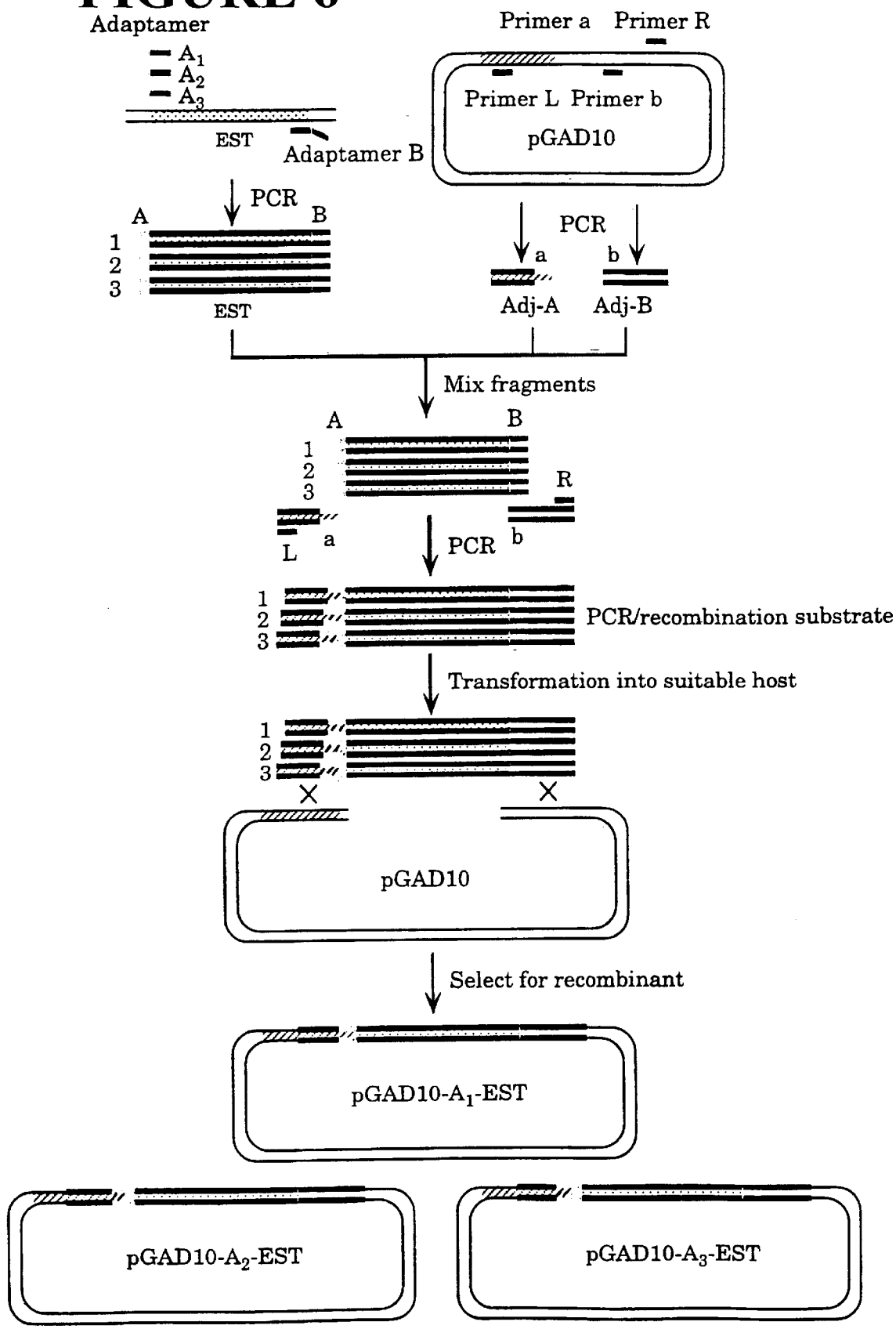
FIG. 6. Use of the four adaptamers shown in FIG. 5 to create an in-frame fusion to a cloned EST. The adaptamers are homologous to sequences outside of the cloned EST. The amplified products are extended by a second round of PCR using Adj-A and Adj-B in the presence of excess primers L and R. The three PCR/recombination substrates are co-transformed with linearized pGAD10 to create the three different clones. Only one of the three clones is fused in-frame, with the Gal4 activation domain.

The adaptamers shown in FIG. 5 have been designed to adapt sequences from the I.M.A.G.E. libraries that have been cloned into the pT7T3-D vector. As described in the brief description of FIG. 5, homology to the sequences adjacent to every clone has been built into each adaptamer. In addition, three sets of adaptamers for the 5' ends have been designed to permit fusion to the 5' end of the ESTs. Using this set of adaptamers for each member of one of these libraries will lead to three different DNA sequence fusions of the EST sequence with the DNA sequence of the Gal4 activation domain of plasmid, pGAD10. One in three of these fusions will be in the correct reading frame resulting in a protein fusion of the EST with the activation domain. The scheme for this is shown in FIG. 6.

The products created from the transformation will be a mixture of all three fusions, one of which will be in-frame with the Gal4 activation domain. As discussed in the previous section, only positive interactions are scored, therefore, the out-of-frame fusions will not disturb a potential positive signal unless the positive clone is under-represented in the mixture. A priori the cloning scheme itself does not present any reason for under-representation of any one sequence.

This entire scheme may be tested and analyzed in two ways. Firstly, a set of adaptamers may be created that will recapitulate the three reading frames using the $Sgs1_{1-795}$ fragment described in the preliminary results section. Twenty separate reactions will be tested. The system will be optimized when 95% of the reactions are positive after all of the steps. The second test will be the PCR/recombination cloning of five ESTs from dbEST. EST representatives that have known two-hybrid interactions may be used. In addition one may amplify the five test ESTs with adaptamer B and adaptamers $A_1$, $A_2$ and $A_3$ separately and pick two clones from each reaction. Thus, a duplicate set of 15 different clones will in effect be created. The efficiency of transformation for adaptamers $A_1$, $A_2$ and $A_3$ should be approximately the same and will be a measure of amplification. In addition, the junction sequences from the 30 clones will be determined by DNA sequence analysis. It is expected that each EST fusion will be as predicted. From these experiments and the experiments described in the previous section on the proportion of correct clones necessary to give a positive, it is clear that the feasibility of this general approach for cloning ORFs from ESTs is a step forward from that of the presently used methods of library construction. (4) Optimization of cDNA Cloning It has already been shown that adaptamers can be designed to permit the cloning of a known mRNA (see preliminary results). However, the efficiency of cloning directly from mRNA was low. In addition to the optimization of this process, there are several questions that must be addressed before this can be used as a general method for constructing clones directly from mRNA. Firstly, how much background noise or signal is there in using all of the transcribed sequences from an organism? Secondly, how much of problem a are partially spliced messages?

To optimize the procedure, one can use three different messages: mouse Rad52, a low abundance mRNA, mouse GAPDH, a moderate abundance mRNA and mouse actin, a high abundance mRNA. One may also use the yeast two-hybrid interaction system. The adaptamers may be designed for each gene to permit cloning into pGAD10. For mouse Rad52, a successful cloning event would result in a fusion protein that can interact with itself fused to the DNA binding domain (pDBD-Rad52 Mm). The first step in the cDNA cloning is reverse transcription. One can simply evaluate this step by standard gel electrophoresis. Next, adaptamers A and B, specific for each gene will be used to synthesize the three genes from the cDNA. This step will also be evaluated via electrophoresis. At this point, the fragments can be gel purified or used directly with Adj-A and Adj-B and primers L and R to generate the recombination fragment. For each mRNA, it would be possible to recover 50 transformants and analyze them by PCR across the insert site of the vector. This step would determine the percentage of transformants with inserts and will assay for size. For Rad52Mm, a map exists of many partially spliced mRNAs. Fragments will be amplified from the different size classes that are observed for DNA sequencing to determine what kind of clone the each size class represents.

Analysis of this small number of genes in great detail will provide the kind of data needed to determine how to proceed. For example, if it is found that only one of the genes gives many different inserts, one would be encouraged to expand the sample to include 20 more genes. One would proceed by analyzing these next 20 genes in great detail to be able to generalize on the kind of results that would be expected. On the other hand, if it is found that two or all three of the original genes give many sized inserts, one would use methods to detect the correct constructs. This may include adding an epitope tag to the C terminus of the amplified cDNA using the 3' adaptamer-B. Addition of such a tag will aid in the identification of full length, intact clones.

Finally, mRNA cloning efforts may be compared with clones from dbEST. For example, often 5' and 3' sequences of an EST are greater than 1000 bp apart. Specific adaptamers will be designed for several of these genes and compared with the efficiency of cloning the gene from newly synthesized cDNA versus from DNA of the pooled cDNA library from which it was isolated. This will aid in the determination of which is the better approach to creating a clone for any specific gene. The ability to use cDNAs will greatly enhance the versatility of this technology and permit it to be expanded to organisms like C. elegans and D. melanogaster, whose genomic sequences are becoming known. Thus interesting guesses and estimations can be made about potential genes and these can be fused directly into two-hybrid vectors via the adaptamers and mRNA cloning described.

EXAMPLE 2

Use of PCR/recombination-directed Library Construction to Create Libraries that will Facilitate Genome-wide Analysis of Yeast This example may be divided into three specific areas of experiments:

(i) A set of unique primers (termed "adaptamers" in this application—see FIG. 1) to every intergenic region on chromosome V will be designed to permit many possible gene fusion, gene disruption and gene insertion strategies. Each adaptamer will have a tag that will allow the fusion of any adjacent sequence by PCR. Using various combinations of adaptamers, two arrayed libraries will be construced.

(ii) The first library will contain the fusion of promoters from every ORF on chromosome V to green fluorescent protein (GFP) gene cloned into a circular autonomously replicating plasmid. Introduction of this library into various strains will permit a "readout" of gene expression for each promoter under different conditions (e.g., various carbon sources, differing osmolarity, after irradiation, etc.) or in different genetic backgrounds (e.g., various deletions such as transcription factors, rad genes, etc.). The library will be transferred from strain to strain by using a kar1 mutation that blocks nuclear fusion but permits the transfer of plasmids or chromosomes between nuclei.

(iii) The second library will contain a gene disruption of each chromosome V ORF in a vector specifically designed to permit the liberation of the disrupting fragment after transfer into the strain of choice. Once again, a kar1 mutant strain will be used as the host strain. In addition, unique restriction sites (I-SceI) and an inducible copy of the I-SceI enzyme will be included in this plasmid. Upon transfer into the recipient nucleus, the I-SceI enzyme will be induced, releasing the disruption fragment and thereby stimulating its integration into the recipient genome.

Background and Significance

The availability of the complete genomic sequences for several organisms provides a challenge and an opportunity to exploit this information creatively. Genome-wide experimental approaches can both facilitate and further the study of biology in these systems with great power. Yeast, being the first sequence-complete eukaryotic organism, combined with its ease of genetic manipulation, offers an ideal system for the development of technologies to explore genome-wide approaches. For example, gene disruptions of every open reading frame in yeast is now possible. However, most strategies invariably construct "static" libraries in a particularly chosen yeast strain. Although valuable, there is a loss of versatility in that the particular needs would not be met for many researchers who would like to introduce a disruption set into a strain(s) containing their unique assay. The next generation of systems to overcome this limitation is described herein. The design of and construction of libraries that can be ported to any strain simply by mating is described. In conjunction with this, methods are described to simplify the construction of an arrayed library using PCR methods and the power of homologous genetic recombination ("PCR/recombination-directed library construction"). The system described is an "open" system: once created, any type of gene fusion can be made in a completely specific, arrayed, genome-wide library. To demonstrate the feasibility of such an approach, disruption of all of the open reading frames on one yeast chromosome may be carried out.

Specifically:

(i) A set of unique adaptamers to every intergenic region on chromosome V will be designed to permit many possible gene fusions, gene disruptions and gene insertion strategies. Each adaptamer will have a tag that will allow the fusion of any adjacent sequence by PCR. Using various combinations of adaptamers, two arrayed libraries will be construced.

(ii) The first library will contain the fusion of promoters from every ORF on chromosome V to green fluorescent protein (GFP) gene cloned into a circular autonomously replicating plasmid. The library will be portable by using a strain containing a kar1 mutation to block nuclear fusion but permit the transfer of plasmids between nuclei. The transfer of this library into various strains will permit a "readout" of gene expression for each promoter under different conditions (e.g., various carbon sources, differing osmolarity, after irradiation, etc.) or in different genetic backgrounds (e.g., various deletions or specific mutations in transcription factors, rad genes, etc.). This will facilitate identification of genes whose regulation changes in response to various conditions or loss of "your favorite gene."

(iii) The second library will contain a gene disruption of each chromosome V ORF in a vector specifically designed to permit the release of the disrupting fragment after transfer into the strain of choice. Once again, a kar1 mutant strain will be used as the host. In addition, unique restriction sites (I-SceI) and an inducible copy of the I-SceI enzyme will be included in this plasmid. Upon transfer into the recipient nucleus, the I-SceI enzyme will be induced, liberating the disruption fragment and thereby stimulating its integration into the recipient genome.

The development of these libraries and demonstration of the feasibility of this approach will lead to the construction of genome-wide libraries. The distribution of such libraries within the research community will provide powerful and flexible tools for all biologists who will be exploring the function of genes. These approaches will also provide a paradigm for studies in other systems that will take place in the future.

Research Design and Methods (1) Adaptamer Design for Intergenic Regions

FIG. 1 illustrates a typical genomic region from yeast. Adaptamers A and B are oriented on each gene's 5' and 3' ends, respectively. The following-design for intergenic adaptamers is set forth: irrespective of gene orientation, each intergenic region is alternately flanked by adaptamer pair C and D followed by adaptamer pair E and F. This design insures that the intergenic regions flanking every gene can be correctly oriented during the PCR fusion steps. C, D, E and will be random sequences that are not found in yeast and do not contain any start codons to avoid premature translation initiation when promoter fusions are made. The priming sequence for the adaptamers will be selected so that the PCR reaction will amplify the entire intergenic region. However, when an intergenic region is large (>1 kb), a second set of adaptamers will be synthesized (shown in FIG. 1 as E' and F' between FUS1 and YCL26C). In such a ease, E and F' are used for FUS1 and E' and F for YCL26C manipulations.

(2) A Promoter Fusion Library

Using exactly the same approach as outlined in the preliminary studies section hereinabove, a promoter fusion library may be be created for all of the genes on chromosome V. Adaptamers for every open reading frame on chromosome V may be synthesized. Each promoter sequence may be PCR-fused with GFP [9] as the reporter gene. This reporter is easy to assay and does not require any sophisticated equipment. Since one goal and embodiment of this application is to make this library easily portable, many labs will be able to utilize the fusions in their favorite strain or mutant background.

Figure 7:
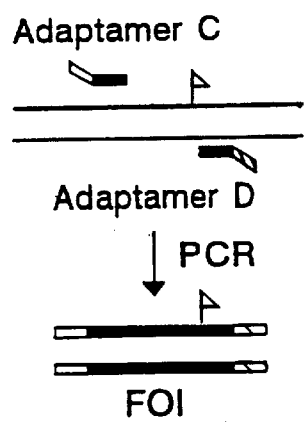
FIG. 7. An outline of the basic steps for making a promoter fusion library using-PCR/recombination. The flag indicates the promoter region of the "fragment of interest" (FOI).
Figure 7:
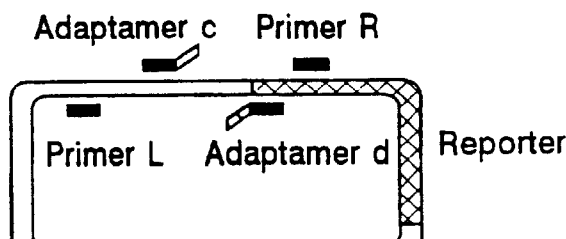
Figure 7:
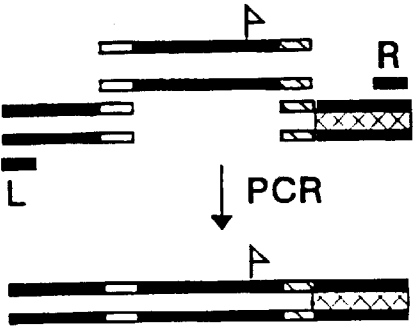
Figure 7:
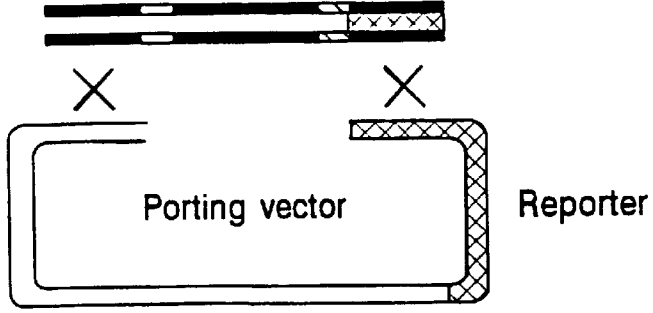
Figure 7:
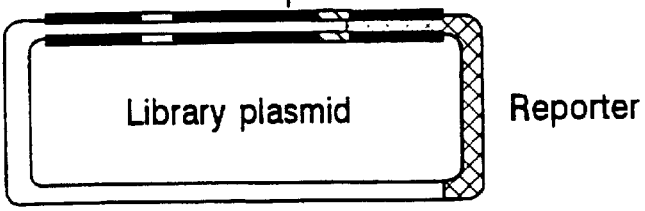

FIG. 7 outlines the basic steps for making the promoter fusion library using PCR/recombination. In the figure, only the synthesis of Adj-C and -D is shown, which is only one of four different combinations Adj-D and -C; Adj-E and -F; Adj-F and -E are the others). Thus, depending on the orientation of the specific promoter, different adaptamers would be used with primers L and R. The synthesis of all of the Adj's will be made in a large batch and used for all of the constructs in the appropriate orientation. PCR amplification may be combined with PCR of the fragment of interest (FOI) with the PCR fusion to pairs of Adj's in one reaction.

Finally, it may be verified that the PCR and subsequent transformation into yeast did not introduce mutations into the GFP reporter gene. For each construct, an amplification of the GFP ORF with one of the primers containing a T7 promoter will be carried out. This fragment will be transcribed and translated in vitro and assayed for fluorescence.

(3) Construction of the Kar1 Donor Strain

Figure 8:
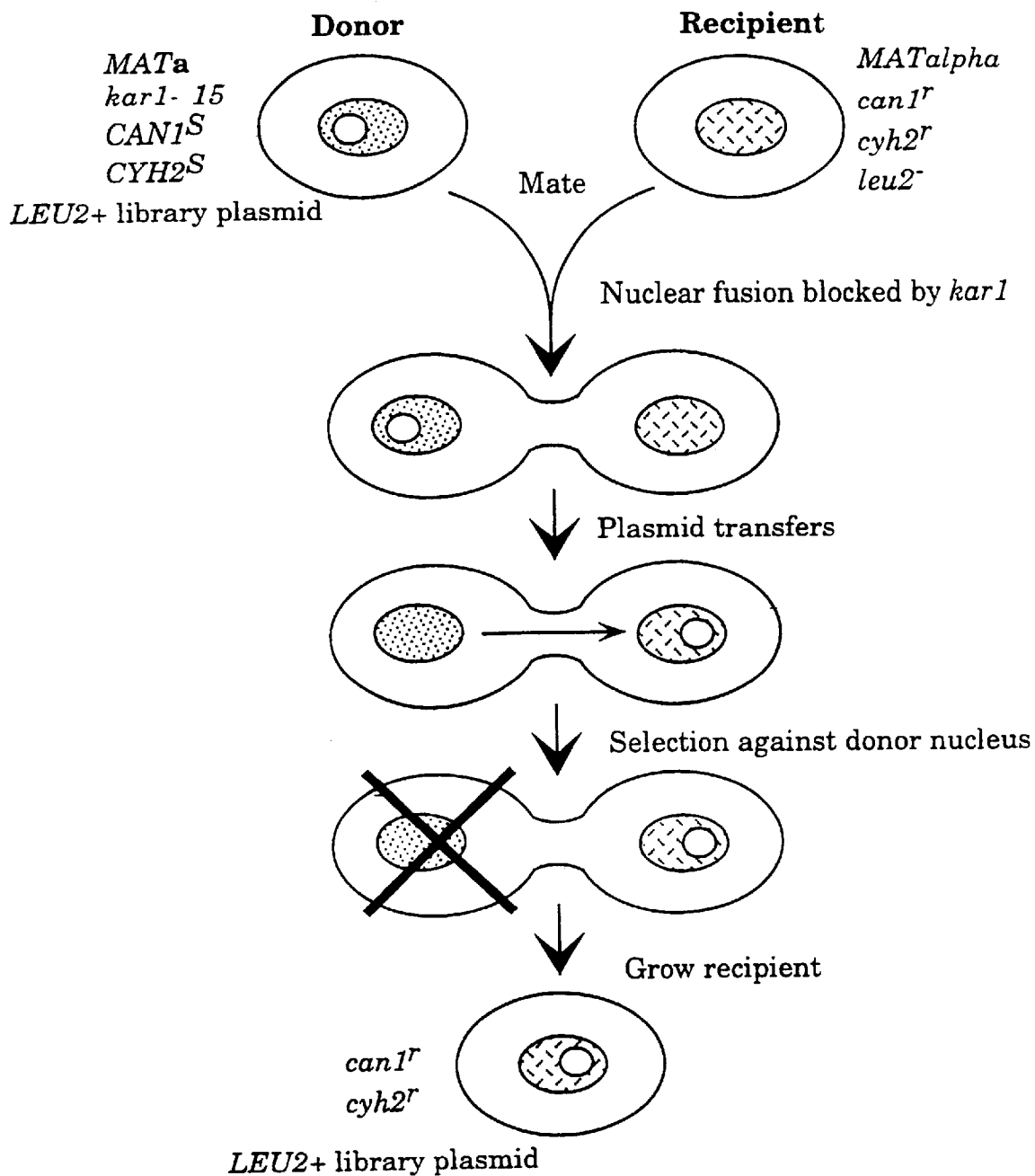
FIG. 8. Illustration of the procedure for kar1-mediated plasmid transfer of a portable promoter fusion library.

The donor strain that will host the library will contain the following relevant genotype: MATa kar1-1Δ15 CAN1_$^s$ leu2-3,112 his3-11, 15 trp1-1 ura3-1. FIG. 8 shows the procedure for kar1-mediated plasmid transfer.

Similar strains have been successfully used for the efficient transfer of yeast artificial chromosomes (YACs) [10]. In such crosses between a donor and recipient, nuclear fusion is rare. However, use of a recessive drug resistant marker, can1 or cyh2, insures that rare nuclear fusions are eliminated by counter-selection. To use this scheme, the recipient strain must be either canavanine resistant or cycloheximide resistant. Since CAN1 is the only gene conferring canavanine sensitivity, can$^r$ mutations can be easily introduced into the recipient strains.

(4) A Portable Gene Disruption Library

Figure 9:
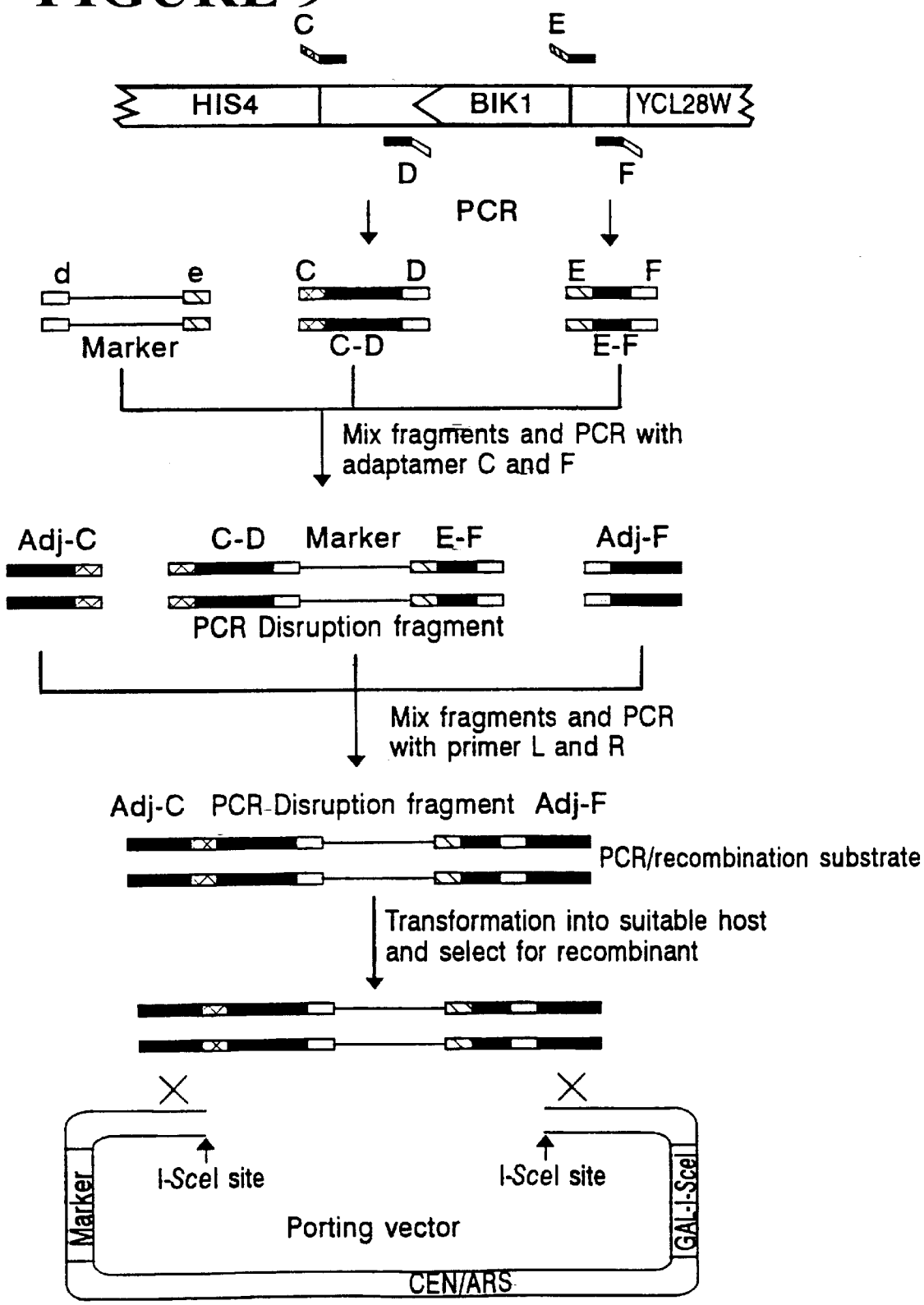
FIG. 9. An outline of a construction of a portable gene disruption library.

The scheme outlined in FIG. 9 will be used to construct a portable gene disruption library. PCR for the intergenic regions will be the same as that described in FIG. 7. Here the need for alternating C, D and E, F adaptamers becomes apparent. Each ORF is flanked by either C–D and E–F or E–F and C–D. Thus, the disruption marker inserted between these fragment pairs must contain adaptamer d, e ends or adaptamer f, c ends. Fusion PCR among the three fragments results in a disruption fragment in the correct genomic orientation. These fragments can be used to transform yeast directly to disrupt the target genes. The *Kluyveromyces lactis* URA3 gene may be used for selection of disruption [11]. This marker does not efficiently recombine with the endogenous *S. cerevisiae* ura3 gene [12] since they only share 70% identity.

This scheme may be taken one step further to create a portable gene disruption library similar to that described for the promoter fusion library. The disruption fragment will be PCR-fused to the appropriate Adj fragments (Adj-C and Adj-F or Adj-E and Adj-D) and co-transformed with the porting vector into the kar1 donor strain described above with the addition of a gal4 mutation to prevent any expression driven by the GAL1 promoter (see below).

The porting vector contains flanking I-SceI restriction sites, and a galactose-inducible I-SceI gene [13, 14]. This enzyme behaves similarly to the HO endonuclease [15]. The advantage over HO is that this rare restriction site does not exist within the yeast nuclear genome (see FIG. 10). After kar1-mediated transfer of the disruption plasmid into the recipient, the I-SceI gene is induced, the disruption fragment is released and homologous recombination occurs leading to a precise chromosomal gene disruption (see FIG. 11). In the case of essential genes, the viability after induction will be very low.

Figure 10:
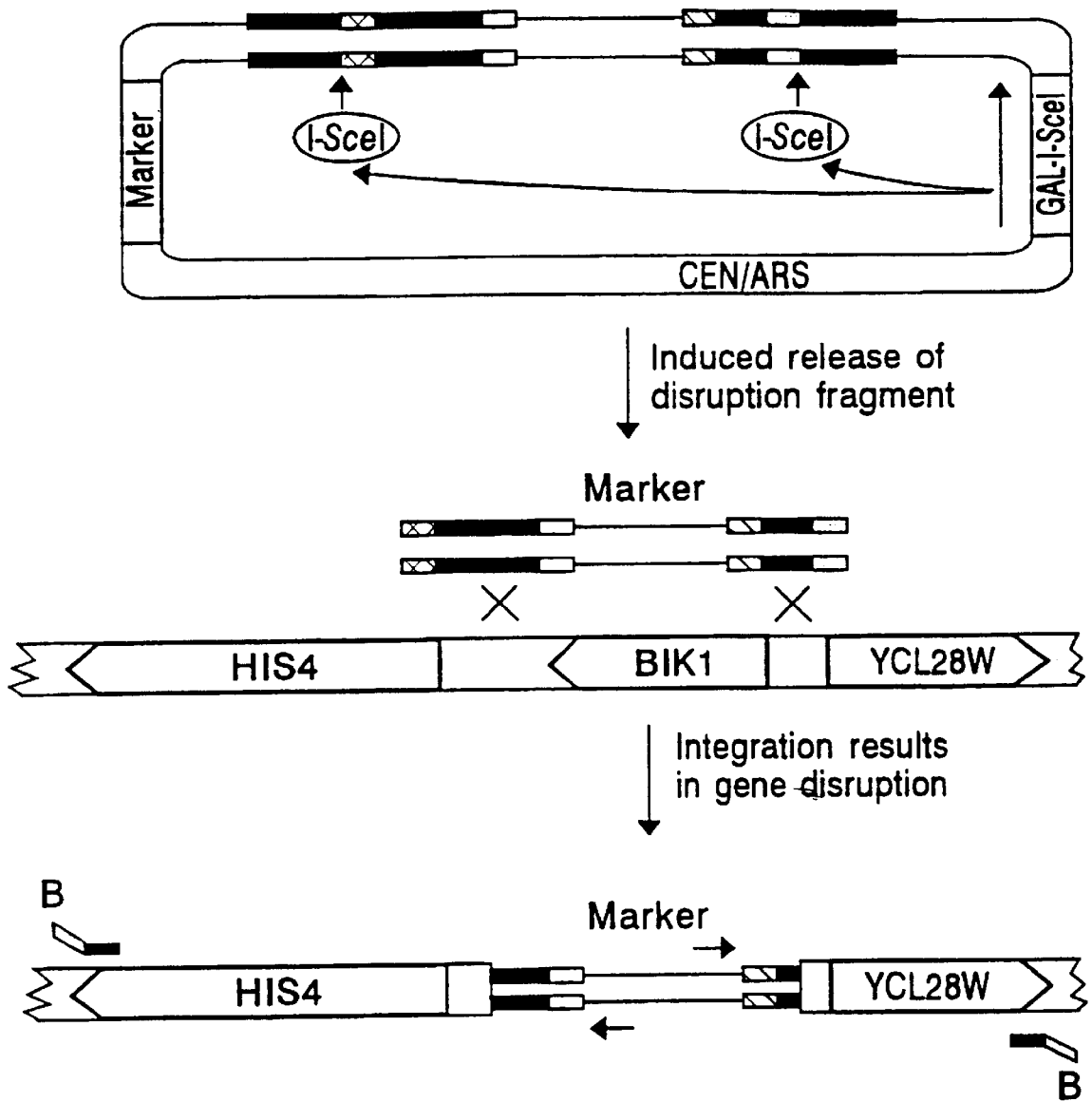
FIG. 10. I-SceI induction of homologous recombination. The primers shown as arrows in the marker are used to confirm correct integration in combination with the adaptamer B.
Figure 11:
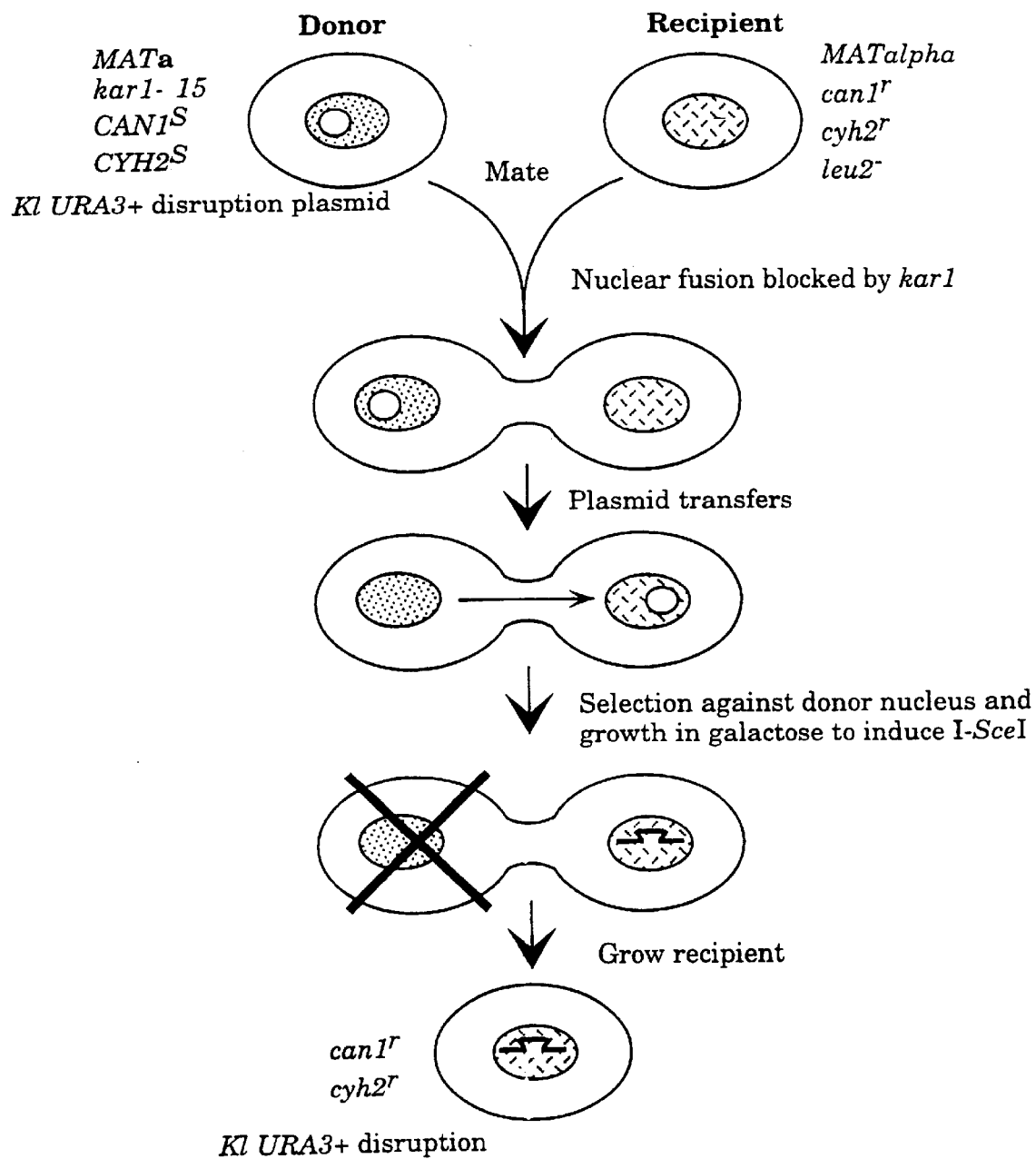
FIG. 11. An illustration of the procedure for kar1-mediated plasmid transfer of a portable gene disruption library.
Figure 12:
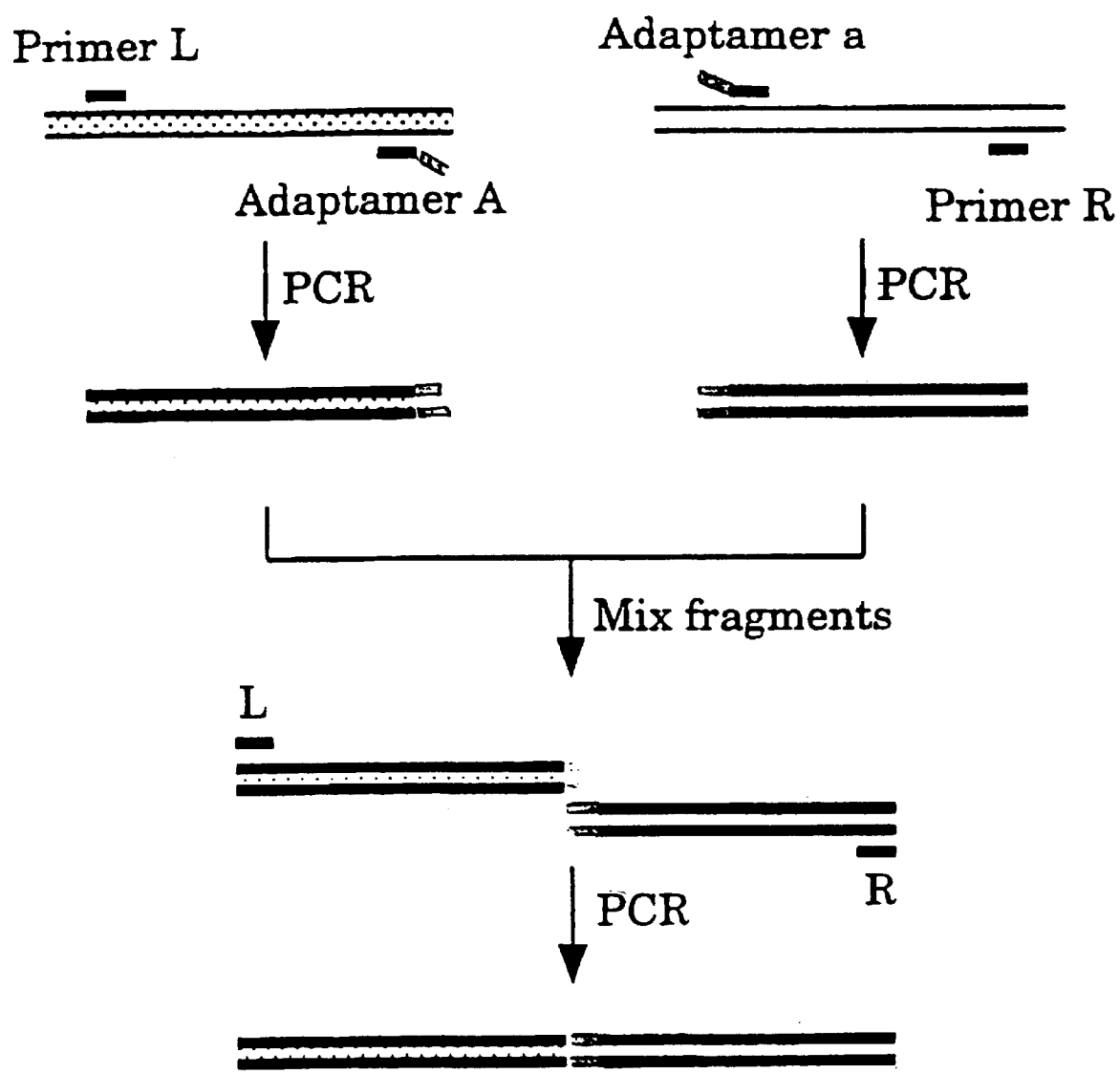
FIG. 12. An illustration of the generation of a directed, fusion recombinant double-stranded nucleic acid molecule. Two polymerase chain reactions (PCRs) are carried out. (1) Primer L and adaptamer A hybridizing to the left (stippled) nucleic acid and generating a PCR product with the right end refecting the sequence of the 5' sequence of adaptamer A. (2) Primer R and adaptamer a hybridizing to the right nucleic acid molecule and producing a product nucleic acid with the left end sequence homologous to the 5' sequence of adaptamer a. The original nucleic acid molecules may be either linear or circular. Adaptamer A and adaptamer a have complementary 5' end sequences. The linear products from (1) and (2) are then mixed together with primer L and primer R and undergo PCR with normal denaturation, hybridization, extension and elongation steps. This final PCR produces at least one nucleic acid which is a directed, fusion recombinant nucleic acid product.
Figure 13:
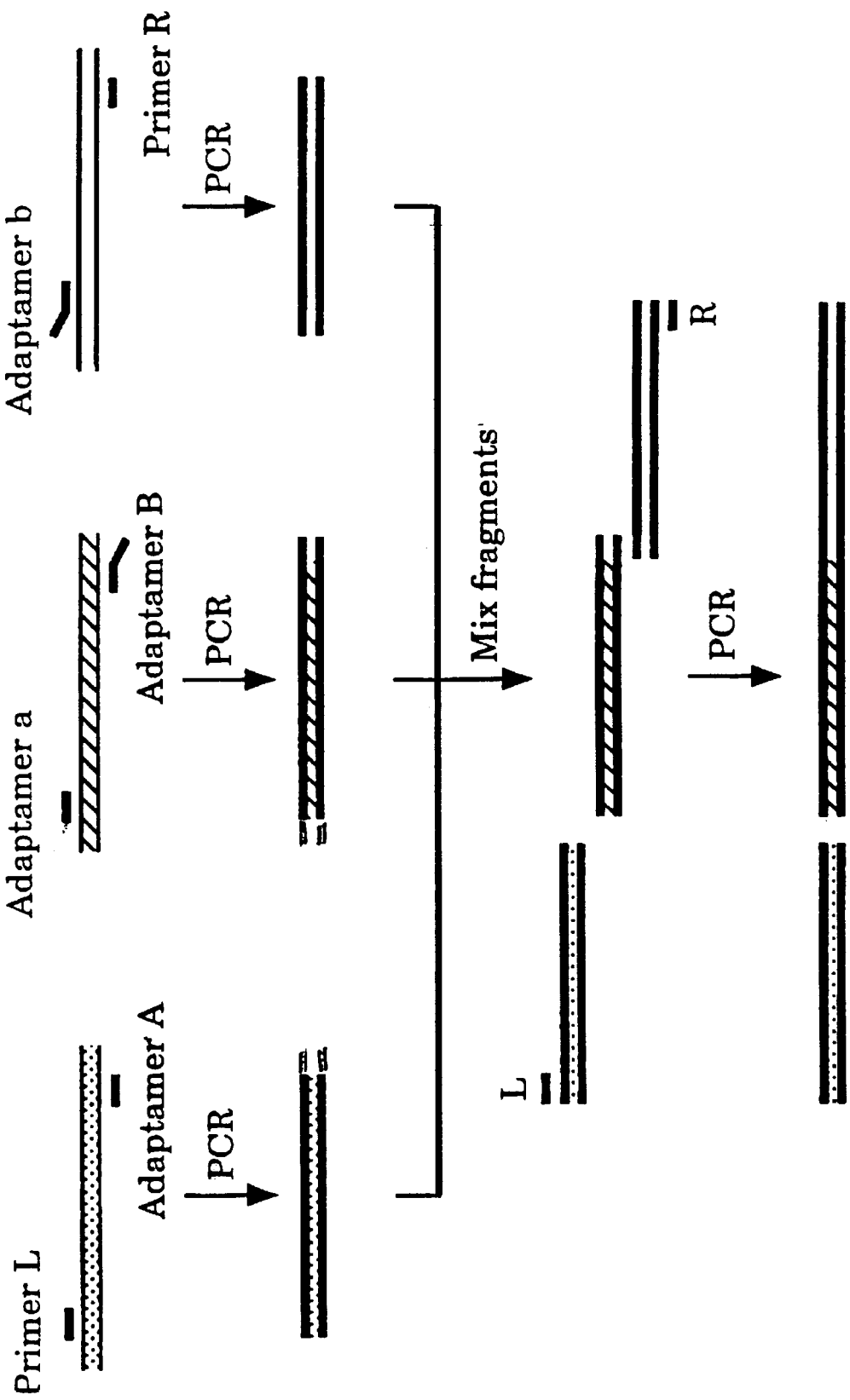
FIG. 13. An illustration-of the generation of a directed, fusion recombinant double-stranded nucleic acid molecule. Three separate PCRs are carried out with each pair-of primers as shown in order to generate at least three linear products as shown. The original nucleic acid molecules may be linear or circular. Each linear product has incorporated the 5' sequence end of the original adaptamer thereby allowing overlap and extension to be possible. The linear products from the three primary PCRs are mixed together with primer R and primer L and undergo normal PCR (denaturation, hybridization, extension and elongation). The second PCR produces at least one linear product that is fusion of the three original nucleic acid molecules. The placement of the adaptamers allows one to engineer the location of each original nucleic acid and the orientation or direction of each nucleic acid in relation to the others. This procedure may be modified to utilize many more nucleic acid molecules. For example one may begin with four original nucleic acids, or five or six or thousands.
Figure 15:
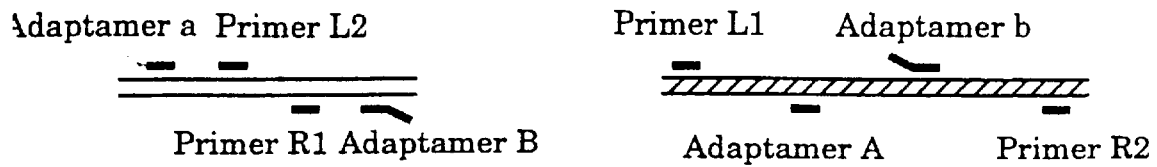
FIG. 15. Use of adaptamers to effect insertion of long foreign nucleic acid molecules into a target nucleic acid molecule and a coincident deletion.
Figure 15:
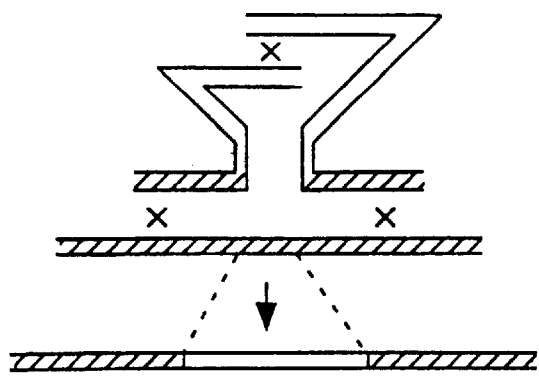
Figure 15:
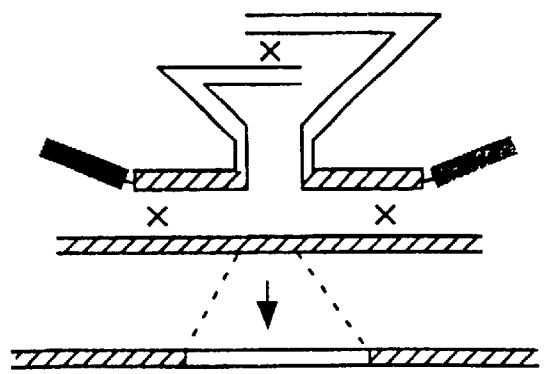

To verify that the gene disruption library in the donor strain is valid, the library may be transferred into a wild type laboratory strain (W303) [161] and examination of the disruptants may be carried out. From previous work, it would be known to one of ordinary skill in the art which genes on chromosome V are essential and they should not grow on galactose. For the others, primers within the disruption marker may be used and the closest adaptamer (A or B in FIG. 3) from either adjacent gene (FIG. 10). Only correct integrations will give the predicted product.

References

1. Orr-Weaver, T. L., J. W. Szostak, and R. J. Rothstein, Yeast transformation: a model system for the study of recombination. Proceedings of the National Academy of Sciences of the United States of America, 1981. 78(10): p. 6354–8.
2. Rothstein, R. J., One-step gene disruption in yeast. Methods in Enzymology, 1983. 101: p. 202–11.
3. Bendixen, C., S. Gangloff, and R. Rothstein, A yeast mating-selection scheme for detection of protein-protein interactions. Nucleic Acids Research, 1994. 22(9): p. 1778–9.

4. Fischer, S. G., et al., A high-resolution annotated physical map of the human chromosome 13q12-13 region containing the breast cancer susceptibility locus BRCA2. Proceedings of the National Academy of Sciences of the United States of America, 1996. 93(2): p. 690–4.
5. Kunes, S., D. Botstein, and M. S. Fox, Synapsis-mediated fusion of free DNA ends forms inverted dimer plasmids in yeast. Genetics, 1990. 124(1): p. 67–80.
6. Ma, H., et al., Plasmid construction by homologous recombination in yeast. Gene, 1987. 58(2-3): p. 201–16.
7. Gangloff, S., et al., The yeast type I topoisomerase Top3 interacts with Sgs1, a DNA helicase homolog: a potential eukaryotic reverse gyrase. Molecular & Cellular Biology, 1994. 14(12): p. 8391–6.
8. Fields, S. and O. Song, A novel genetic system to detect protein-protein. interactions. Nature, 1989. 340(6230): p. 245–6.
9. Chalfie, M., et al., Green fluorescent protein as a marker for gene expression. Science, 1994. 263(5148): p. 802–5.
10. Spencer, F., et al., Yeast kar1 mutants provide an effective method for YAC transfer to new hosts. Genomics, 1994. 22(1): p. 118–26.
11. Shuster, J. R., D. Moyer, and B. Irvine, Sequence of the *Kluyveromyces lactis* URA3 gene. Nucleic Acids Research, 1987. 15(20): p. 8573.
12. Rose, M., P. Grisafi, and D. Botstein, Structure and function of the yeast URA3 gene: expression in *Escherichia coli*. Gene, 1984. 29(1-2): p. 113–24.
13. Plessis, A., et al., Site-specific recombination determined by I-SceI, a mitochondrial group I intro-encoded endonuclease expressed in the yeast nucleus. Genetics, 1992. 130(3): p. 451–60.
14. Choulika, A., et al., Induction of homologous recombination in mammalian chromosomes by using the I-SceI system of *Saccharomyces cerevisiae*. Molecular & Cellular Biology, 1995. 15(4): p. 1968–73.
15. Kostriken, R., et al., A site-specific endonuclease essential for mating-type switching in *Saccharomyces cerevisiae*. Cell, 1983. 35(1): p. 167–74.
16. Thomas, B. J. and R. Rothstein, Elevated recombination rates in transcriptionally active DNA. Cell, 1989. 56(4): p. 619–30.

EXAMPLE 3
Cloning-free PCR-based Allele Replacement Methods

Efficient homologous recombination permits the directed introduction of specific mutations into the yeast genome. Here a cloning-free, PCR-based allele replacement method is described that simplifies allele transfer between yeast strains. The desired allele from one strain is amplified by PCR along with a selectable/counter-selectable marker. After transformation, the resident allele in the target strain is replaced by creating a duplication of the new allele. Selection for direct repeat recombinants results in a single copy of the new allele in the target strain. Specifically, the desired allele is amplified by PCR with a pair of adaptamers, which are chimeric oligonucleotides that are used to amplify the allele and differentially tag its 5' and 3' ends. These tags allow the directed fusion to two different, but overlapping regions of an appropriately tagged selectable/counter-selectable marker after a second round of PCR amplification. Following co-transformation of the two fusion fragments into yeast, homologous recombination efficiently generates a duplication of the amplified allele flanking the intact selectable marker in the genome. After counter-selection, only the desired allele is retained as a result of direct repeat recombination. A simple modification of this method allows the creation of de novo mutations in the genome.

Introduction

To understand the biological role of a gene, it is often necessary to study different alleles to identify distinct functions. Frequently mutant alleles are isolated in diverse genetic backgrounds. To ensure that a phenotype is due to a specific mutation, it is advantageous to analyze alleles in an isogenic strain background. Therefore, it is useful to be able to transfer specific mutations between different strains. In addition, in the case of conserved genes, informative alleles may even exist in different organisms. Consequently, it is desirable to be able to introduce a similar mutation into the homolog of a genetically tractable organism to analyze its phenotype in vivo. *Saccharomyces cerevisiae* has proved to be an ideal genetic system for these studies. Here, we take advantage of efficient homologous recombination in yeast to develop new approaches to introduce specific mutations into the genome.

Most current allele transfer methods are based on the pioneering work of Scherer and Davis (1979). An allele on a plasmid is integrated at its chromosomal locus creating a duplication where one copy contains the new allele ("pop-in"). After a subsequent direct repeat recombination event, either the introduced or the resident allele remains in the genome ("pop-out"). To construct the plasmid, the desired allele must be: (1) derived from a fragment cloned from its original strain, (2) transferred on the plasmid by gap-repair (Orr-Weaver et al. 1983) or (3) cloned onto the plasmid after PCR amplification from the genome. To create a new mutation, the wild type yeast gene sequence must be specifically altered, e.g., using an *E. coli*-based mutagenesis system (Sambrook et al. 1989). The main disadvantages of classical "pop-in" "pop-out" recombination are that it requires cloning steps tailored for each allele and that the position of the cross-over in the direct repeat recombination event determines whether or not the plasmid-borne mutation remains in the genome.

Recently, two methods have been described for transferring specific alleles into the yeast genome (Längle-Rouault and Jacobs 1995; Schneider et al. 1995). In both methods, a single round of PCR is used to generate a linear fragment that contains a short region of the gene sequence as two direct repeats flanking a selectable/counter-selectable marker. Both repeats carry the desired mutation and upon transformation, the linear fragment creates a duplication of the short sequence where, ideally, the two copies in the genome contain the mutation. The advantages of these methods are that any mutation can be created easily using PCR primers without any need for cloning. Furthermore, for integrants where both copies of the duplication retain the mutation, the subsequent pop-out event always preserves the desired mutation in the genome. However, these approaches have four disadvantages:

(1) Integration occurs at low frequencies since short stretches of homologous sequences are used to target the mutant allele. (2) The frequency of the subsequent direct repeat recombination event is also very low since the direct repeat is short. (3) The use of short sequences often results in the failure to incorporate the desired mutation into both repeats. (4) The integration almost always creates a gene disruption, making this method cumbersome for essential genes.

In this example, an improved PCR-mediated approach is described that overcomes many limitations of previous allele replacement methods. Specifically, long regions of homology are generated that significantly increase the frequencies of both the integration and subsequent direct repeat recombination events. In addition, the resident chromosomal copy is almost always deleted from the genome. This method can also be applied to transfer alleles into any essential gene, even in haploid cells, as long as the mutation itself does not cause lethality. Finally, an additional advantage is that successful integrants directly exhibit the phenotype of the altered allele, even before selection of pop-out recombinants.

Figure 18:
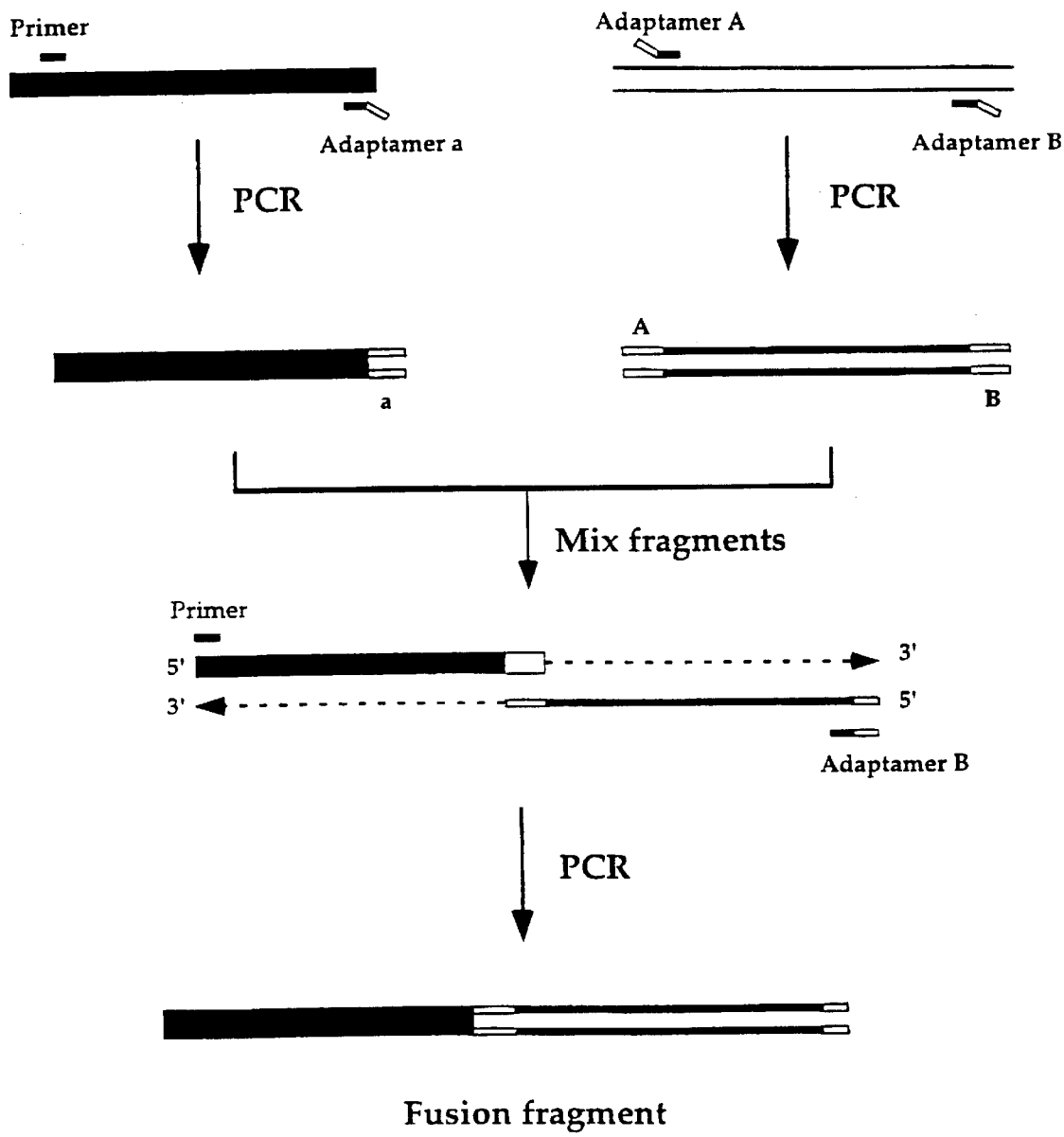
FIG. 18. Use of adaptamers to fuse two fragments. The matched adaptamers A and a contain complementary sequence tags at their 5' ends as described in the text (indicated as "A" and "a" on the PCR products). The 3' ends of each adaptamer are homologous to two different DNA sequences, respectively. Adaptamer A, in conjunction with adaptamer B, differentially tag one fragment at each end. The "primer" is designed to permit the PCR amplification of the other fragment as shown in the figure. After amplification, the fragments are mixed and excess primer and adaptamer B are added for an additional PCR step. The complementary sequence tags in adaptamers A and a direct the fusion of the two fragments leading to a chimeric product.

Results: A New Allele Replacement Method A new approach for allele replacement is described that utilizes "adaptamers," which are chimeric oligonucleotides complementary to two different DNA sequences. The fusion of two fragments is facilitated by using a pair of "matched" adaptamers (A and a in FIG. 18), which contain complementary sequences at their 5' ends. In the example shown in FIG. 18, adaptamers A and B are used in a PCR to amplify a fragment and tag its 5' and 3' ends. In a separate PCR, the matching adaptamer a is used to tag a second fragment. Subsequently, these two fragments are mixed with a suitable primer and adaptamer. During PCR annealing at the matched ends results in a fused molecule.

Figure 19:
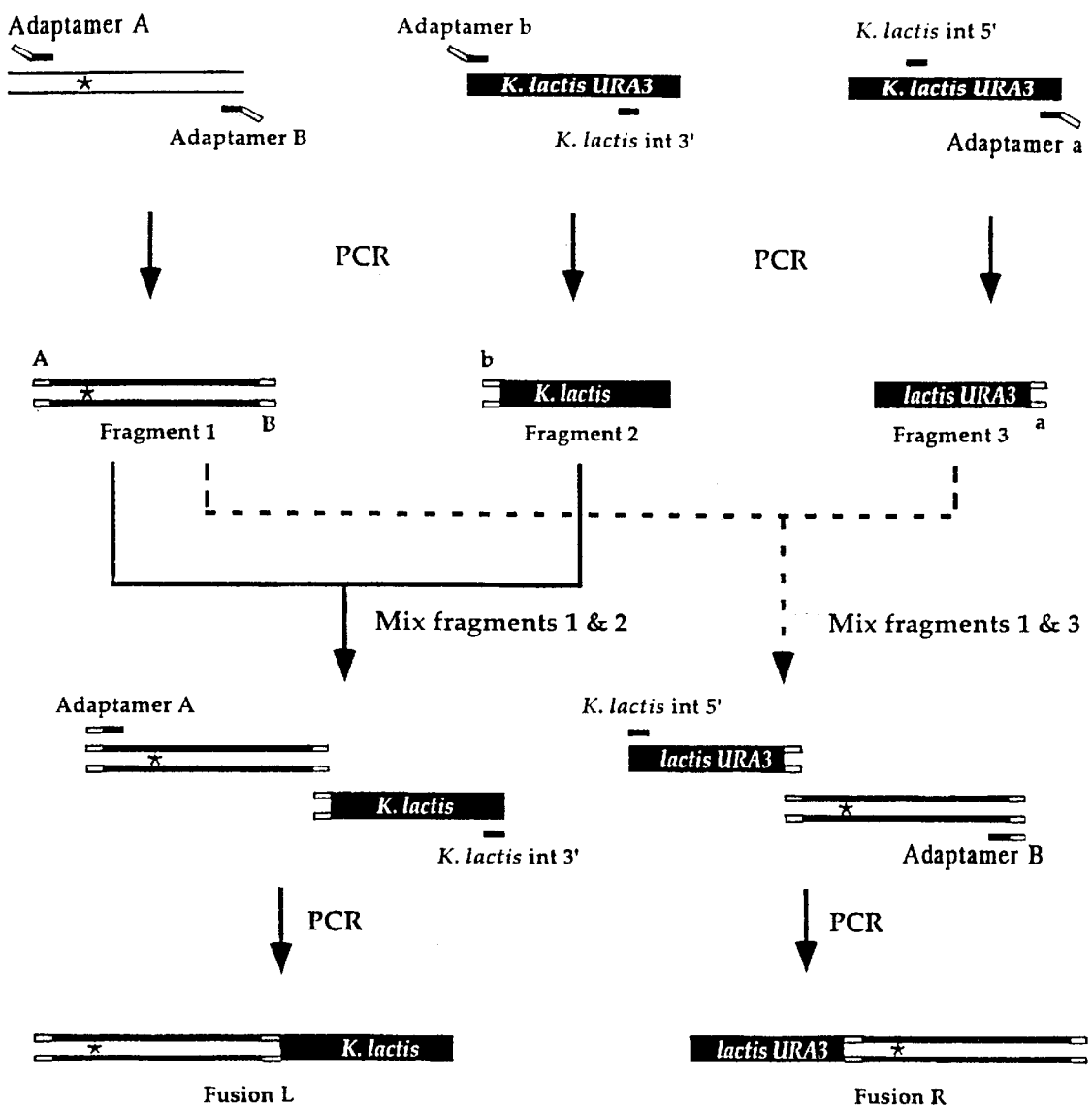
FIG. 19. Generating fusion fragments for allele replacement. The gene of interest with an altered site (indicated by an "*") is amplified by PCR using adaptamers A and B (fragment 1). Similarly, two overlapping K. lactis URA3 fragments are generated separately by PCR with the K. lactis URA3 adaptamers and two internal K. lactis URA3 primers (fragments 2 & 3). Fragments 2 & 3 do not encode full-length URA3 and thus, are represented as "K. lactis" and "lactis URA3," respectively. The ends tagged by the adaptamers A, B, a and b are labelled on the initial PCR products. As described in FIG. 1, fragments 1 and 2 are mixed with the K. lactis in 3' primer and adaptamer A for an additional PCR step to generated a new fusion product (fusion L). In a separate PCR, fragments 1 and 3 are mixed with the K. lactis int 5' primer and adaptamer B to generate a second chimeric fragment (fusion R). Both fusion L and R contain the altered site.

To create the fragments for allele replacement, two sets of matching adaptamers are synthesized (adaptamers A/a and B/b). As shown in FIG. 19, a fragment containing the desired allele is amplified using adaptamers A and B (fragment 1). Two truncated, overlapping fragments of a selectable/counterselectable marker (*Kluyveromyces lactis* URA3) are tagged with the matching adaptamers b and a, respectively (fragments 2 & 3). These two fragments are fused separately with fragment 1 to create fusion L and fusion R after a second round of PCR. Rare, random insertions of each fusion fragment alone into the genome will not generate a functional marker (Schiestl et al. 1993). On the other hand, homologous recombination between the overlapping selectable marker fragments reconstitutes the functional marker (Ma et al. 1987). The *K. lactis* URA3 gene is used to reduce undesired gene conversion events between the transforming DNA and the endogenous *S. cerevisiae* ura3 gene (Bailis and Rothstein 1990), since they only display 71% identity (Shuster et al. 1987).

Figure 20:
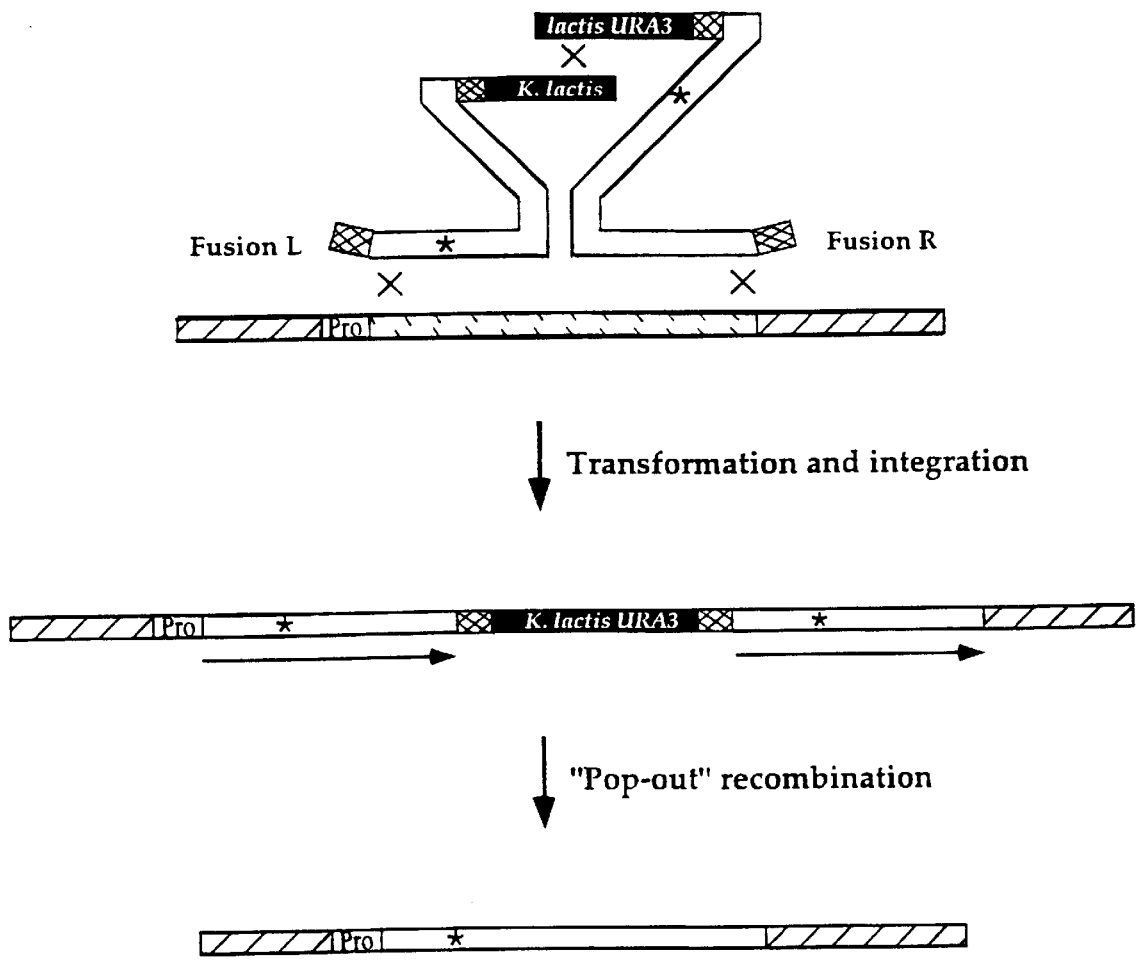
FIG. 20. Integration of fusion fragments and subsequent pop-out event for allele replacement. Fusion L and R (FIG. 2) are co-transformed into the appropriate yeast strain. Recombination between the two fusion fragments generates a functional, intact K. lactis URA3 gene. Recombination between each fragment and the homologous chromosomal locus results in a duplication of the gene of interest where both copies contain the altered site ("*"). During the integration, the tags are deleted from the ends of the fragments. The "left" copy of the duplication lies adjacent to the endogenous promoter (purple box labelled "Pro"). After the subsequent pop-out event, the altered site is always preserved in the genome.

To generate a direct repeat of the desired allele flanking the intact selectable marker, approximately 100 ng of each fusion fragment are co-transformed into yeast (FIG. 20). Generally, 25 to 100 transformants are obtained, all containing the recombined fragments integrated at the correct chromosomal target locus. The final step requires a pop-out of the direct repeats to leave a single altered copy in the genome. Since the direct repeats are gene-length ($\approx$300 to $\approx$3000 bp), the efficiency of recombination is high ($10^{-3}$ to $10^{-4}$) and recombinants are easily selected on 5-fluoro-orotic acid (5-FOA) medium (Boeke et al. 1987).

This method requires the synthesis of six primers: two are gene-specific and four may be reused for additional allele transfer experiments. The first pair (adaptamers A and B) are $\approx$40-mers used to amplify the open reading frame (ORF) of the desired allele. Adaptamer A contains a unique 20 bp tag at its 5' end followed by 20 or 21 bp that are identical to the 5' end of the ORF starting from the ATG start codon. Adaptamer B consists of a unique 20 bp tag followed by 20 bp of the reverse complement of the 3' end of the ORF including the termination codon sequence. The remaining four primers for amplifying the two partial *K. lactis* URA3 fragments are adaptamers (a and b) and two internal primers. The first 20 bp of adaptamer a contains the reverse complement of the unique tag of adaptamer A followed by 20 bp of the reverse complement of the 3' end of *K. lactis* URA3 197 bp downstream from the termination codon. The 5' end of adaptamer b contains the 20 bp reverse complement of the unique tag of adaptamer B followed by 20 bp identical to the sequence starting 283 bp upstream of the ATG start codon of *K. lactis* is URA3. In addition, two internal primers for *K. lactis* URA3 were designed. One (5'-internal) contains the identical 25 bp starting 105 bp downstream from the *K. lactis* URA3 start codon. The other (3'-internal) contains the reverse complement of the *K. lactis* URA3 sequence 552 bp downstream of the ATG. These last four primers are common to every allele replacement and need to be synthesized only once. In addition, pairs of adaptamers (A and B) for every yeast open-reading frame are commercially available (Research Genetics, Huntsville, Ala.).

The Efficiency of the Method

To test the efficiency of the allele replacement method, it was applied to two essential genes: RFA1 and KAR1. Mutations in each gene cause an easily detectable phenotype. rfa1-D228Y mutant strains display increased UV sensitivity and exhibit increased direct repeat recombination (Smith and Rothstein 1995). The rfa1-D228Y mutation is located near the middle of the 1866 bp ORF at position 682 and creates a new AccI restriction site. To transfer this mutation into W303-1A, a wild type yeast strain, adaptamers A and B for RFA1 were used to amplify the full-length rfa1-D228Y mutant allele. This fragment was fused separately to the two overlapping URA3 fragments described above and in FIG. 19. 100 ng of the chimeric fragments were co-transformed into the wild type strain and 25 URA$^+$ transformants were obtained. All 25 transformants displayed increased UV sensitivity. This phenotype indicates that the left repeat contains the full-length copy of the mutated ORF as it is adjacent to its native promoter. Subsequent PCR analysis followed by the diagnostic restriction enzyme digestion (AccI) showed that both repeats contained the rfa1-D228Y mutation. The absence of wild type information shows that each transformant integrated at the chromosomal RFA1 locus. Five transformants were chosen for further analysis. Direct repeat recombination events were selected and occurred at frequency of $10^{-3}$. In each case, the event led to loss of the *K. lactis* URA3 marker and preserved a single copy of the rfa1-D228Y allele in the genome as shown by PCR analysis.

Next, the feasibility of this method was tested at the KAR1 locus. kar1 is a mutant defective in nuclear fusion (Conde and Fink 1976) resulting from an C to T transition at position 450. Similarly, the kar1 mutant allele was fused with the *K. lactis* URA3 fragments and the resulting PCR products were co-transformed into a wild type strain selecting for URA$^+$ transformants. The transformation efficiency was similar to that found for rfa1-D228Y and all 25 transformants carried the kar1 allele on the left repeat as determined by their defect in diploid formation. Pop-out recombinants were selected on 5-FOA medium for 5 of the transformants. Twenty recombinants from each exhibited a defect in diploid formation. The failure to recover any recombinants exhibiting wild type mating behavior suggests that the mutation was incorporated into the second repeat as well.

Finally, it was determined that the allele transfer method also works for deletion alleles. The kar1-Δ15 allele was used since it carries a 255 bp deletion in the KAR1 ORF (Spencer et al. 1994). After transformation of the two fused fragments, 100 transformants were obtained on uracil deficient medium. All of the transformants exhibited a defect in diploid formation showing that they carried the kar1-Δ15 mutation on the left repeat. Ten of these transformants were tested for the presence of the kar1-Δ15 mutation in the second repeat by examining the mating behavior after the pop-out event. Similar to that observed for kar1-1, all of the recombinants exhibited a defect in diploid formation indicating that the kar1-Δ5 mutation was likely present in the second repeat. These results demonstrate that the allele transfer method is applicable to deletion mutations as well as point mutations.

Efficiency of Transfer of Sequences that are Close to the Adaptamer

For some genes, the desired site may be located very close to the 5' or the 3' end of the gene of interest. Since sequences adjacent to the extreme 5' and 3' ends of the two fusion fragments may not be incorporated during integration as a result of the position of the crossover, the integration event may not result in the duplication of the allele. It was determined the efficiency of allele transfer by examining the frequency of successful integration of the site as a function of distance from the adaptamer. The rfa1-D228Y allele was used as a test system since the mutation can easily be detected by colony PCR (Huxley et al. 1990; Ling et al. 1995).

Four new adaptamers, designated A1, A21, A61 and A81, annealing 20, 40, 80 and 100 nucleotides, respectively, from the mutant site were designed for transferring the rfa1-D228Y allele. In combination with adaptamer B, the four fragments were amplified from the rfa1-D228Y mutant strain. Including the nucleotides in the adaptamer, the mutation is 21, 41, 81 and 101 nucleotides from the end of the region of homology on the amplified fragment. After fusion with the K. lactis URA3 fragments, the resulting four pairs of fragments were separately co-transformed into the wild type strain. All of the URA3+ transformants contain duplications of the amplified RFA1 region. Next, both repeats were analyzed for the presence of the rfa1-D228Y allele and the results are summarized in Table P. Data is also included for the full length RFA1 fragment, where there is 681 bp of homology from the 5' end to the mutation. Nearly 100% of the transformants contained the rfa1-D228Y mutation in both repeats when the mutation is located 81, 101 or 682 bp downstream from the 5' end of the homologous sequence. Surprisingly, even when the homologous sequence upstream of the mutation was reduced to 21 bp and 41 bp, 30–50% of the transformants contained the mutation in both repeats.

A Modification of the Method Allows the Creation of de novo Mutations

Figure 21:
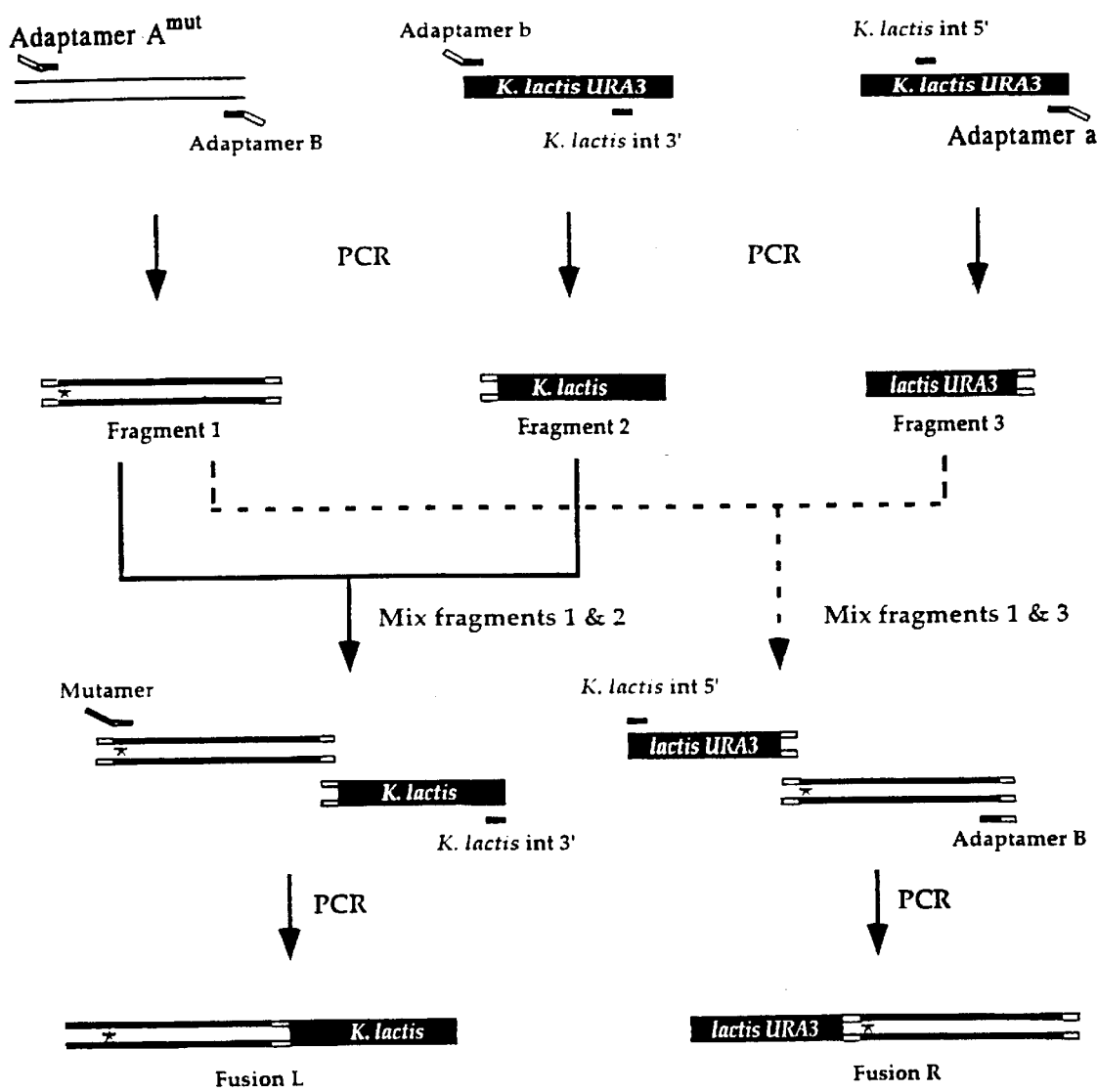
FIG. 21. Use of adaptamer $A^{mut}$ and a mutamer to create a de novo mutation. Adaptamer $A^{mut}$ contains the sequence tag described for adaptamer A (see text) followed by an altered nucleotide(s) (indicated by the blue dot on adaptamer $A^{mut}$) and an additional 20 bp of sequence adjacent to the desired change. In combination with adaptamer B, PCR is used to generate mutated fragment 1. As described in FIG. 19, fragment 1 is fused to fragment 3 generating fusion R. To create fusion L, fragments 1 and 2 are mixed with K. lactis int 3' and a mutamer. The mutamer consists of an additional 17 bp of sequence upstream of the desired change followed by the desired change itself and 14 bp downstream. The "*" depicts the introduced mutation. Fusions L and R recombine as described in FIG. 20.

The allele replacement method described here can also be modified to create directed mutations in any gene. For this purpose, two new primers are designed. One is an adaptamer ($A^{mut}$ or $B^{mut}$) that contains the desired mutation (shown as a blue dot in adaptamer $A^{mut}$ in FIG. 21) immediately following the unique sequence tag. The other primer is called a "mutamer" and is used in a second round of PCR to extend the homology to facilitate integration of the mutation. A convenient length for the mutamer is 35 to 60 bp. The 5' nucleotides, which typically can vary from 20–45 bp, are used to extend homology upstream of the mutant site. In the example shown in FIG. 21, adaptamers $A_{mut}$ and B are used to amplify and incorporate the desired mutation into a fragment using the wild type gene of interest as the template. The fusion fragments are generated as described for the allele transfer method except that the the mutamer is substituted for the adaptamer $A^{mut}$ during the amplification of the fusion fragment L. The additional nucleotides added from the mutamer effectively extends the region of homology adjacent to the mutated site to insure its incorporation into the genome. As before, transformation of the two fusion fragments results in a direct repeat in which, ideally, the mutation is duplicated at its genomic locus.

This method was used to create a lysine to arginine missense mutation at amino acid position 706 (K706R) within the conserved Walker box of the Sgs1 helicase (Gangloff et al. 1994; Lu et al. 1996). The mutation was also designed to introduce a new BglII site facilitating its detection. Adaptamer $A^{mut}$ contains the same adaptamer $A^{mut}$ tag sequence described before and the appropriate nucleotide change for the sgs1 mutation (A to G) along with 19 bp of downstream sequence. The mutamer contains 17 bp upstream of the G followed by 14 bp downstream of the mutant site. Using adaptamer $A^{mut}$ and adaptamer B, the C-terminal half of the SGS1 gene sequence from the K706R mutation to its stop codon was amplified by PCR. As described above, two fusion fragments were generated and after co-transformation, 45 transformants were obtained. Colony PCR analysis followed by BglII digestion indicated that almost 25% of the transformants (11) contained the sgs1-K706R allele in both copies of the duplication. This efficiency, using 17 nucleotides of extended homology, is comparable to that found when 20 nucleotides were placed upstream of the rfa1-D228Y mutation (30% showed duplication of the mutation, Table P).

Discussion

In this example, a new method is described that considerably improves existing allele replacement methods and can be modified to permit directed mutagenesis of any site within the yeast genome. One of the major advantages of this method is that no cloning steps are necessary. In addition, many of the required reagents are commercially available. Compared to previously described PCR-based allele replacement methods (Langle-Rouault and Jacobs 1995; Schneider, et al. 1995), the integration and subsequent pop-out recombination frequencies are elevated at least two orders of magnitude due to the increased length of homology. Another important advantage of this method is that, after integration, both copies of the duplicated gene carry the alteration. This ensures that the mutation will always be preserved in the genome after the subsequent pop-out event, thereby eliminating further screening of recombinants. Moreover, in most instances, the effects of a specific alteration can be assessed immediately after transformation since one altered copy recombines adjacent to its endogenous promoter. Lastly, with this allele replacement method, integration of the fusion fragments into the genome does not create a gene disruption (Shortle et al. 1982), which often occurs with the other PCR-based methods. Therefore, the adaptamer method can be used for allele transfer into essential genes in haploid cells provided that the mutation itself does not create a lethal phenotype.

As is the case with other PCR-based methods, undesired second site mutations may be generated by polymerase errors during the PCR amplification. However, this problem can be addressed by using high fidelity polymerases like Pfu (Stratagene) or Pwo (Boehringer-Mannheim), where the error frequencies of these enzymes are much lower than that of Taq polymerase (Barnes 1992), and/or by keeping the number of PCR cycles at a minimum during amplification. In addition, a new technique has been described that uses the mismatch repair complex from E. coli, the MutHLS proteins to remove the mistakes from PCR products (Smith and Modrich 1997). Finally, it is always advisable to compare the phenotype of several transformants to ensure that the effect is due to the allele of interest and not caused by a secondary mutation.

Figure 22A:
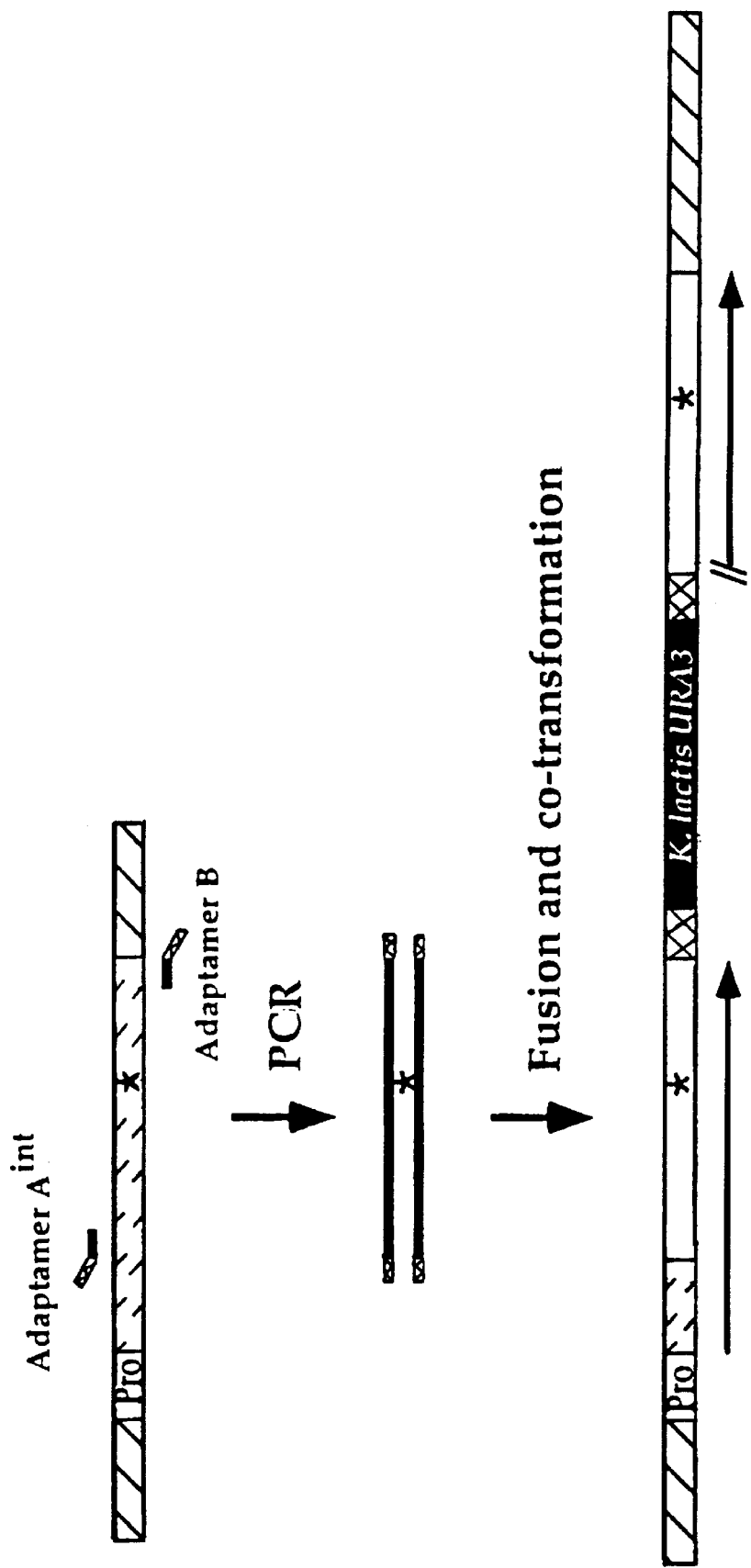
FIGS. 22A–22B. Fragmentation of large sequences for allele transfer.
Figure 22B:
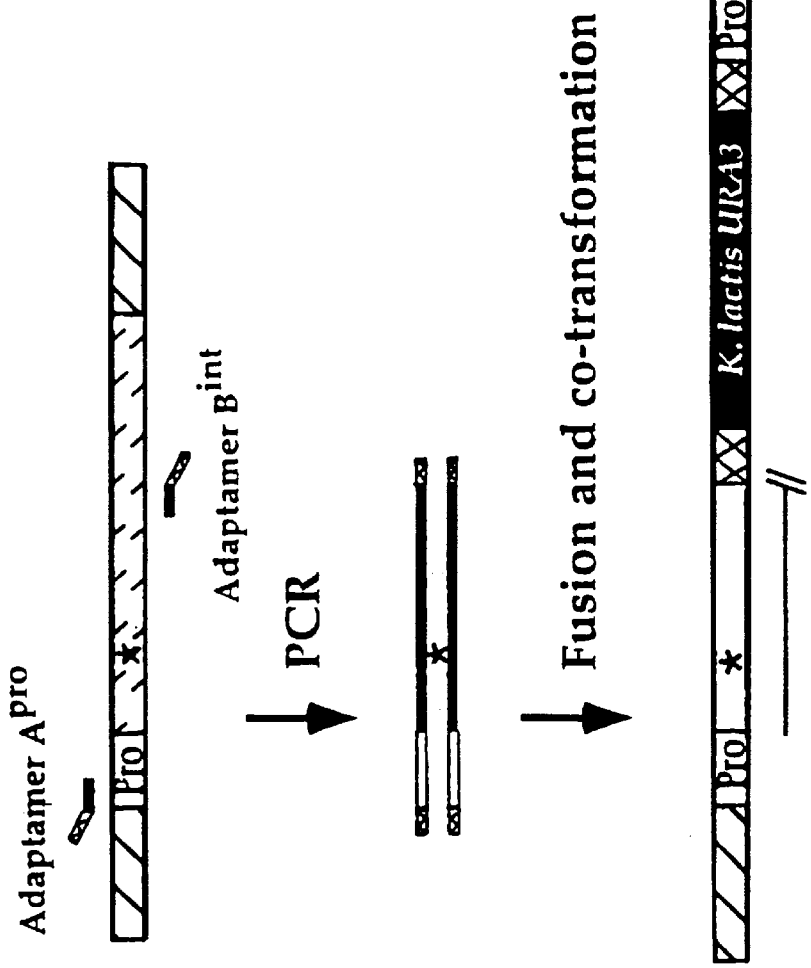

It was demonstrated that this method works successfully when the length of the amplified fragment is up to 3.1 kb (sgs1-K706R). In principal, even longer fragments should easily be amplified with improved enzymes (e.g., LA Taq polymerase (TaKaRa Biochemicals), rTth DNA Polymerase (Perkin-Elmer)). However, an alternative solution for longer ORFs is readily available by simply fragmenting the gene of interest (see FIG. 22A). This requires the synthesis of a new adaptamer. The choice of which of the two adaptamers to replace depends upon the position of the desired site within the ORF. When the site lies nearer to the 3' end, a new adaptamer $A^{int}$ (defined as an internal position in the ORF) is designed (FIG. 22A). In conjunction with adaptamer B, a shorter 3' fragment of the gene is amplified. After fusion to the *K. lactis* URA3 fragments and subsequent transformation, the resulting integration only duplicates the 3' fragment but does not create a gene disruption (see FIG. 22A). When the desired site is closer to the 5' end of the ORF, a new adaptamer $B^{int}$, is used with adaptamer A (FIG. 22B). After integration, a gene disruption will be created since the resulting duplication of this shortened 5' amplified fragment gives rise to one 3' truncated copy and one promoterless copy of the gene. To circumvent gene disruption when the gene of interest is essential, the 5' end of the duplicated fragment can be expanded to include the promoter. This requires the synthesis of a new adaptamer $A^{pro}$ (defined by sequences upstream of the ORF) that permits amplification of the promoter (FIG. 22B). When adaptamer $A^{pro}$ is used in combination with the adaptamer $B^{int}$, the promoter region also will be duplicated resulting in a full-length copy of the gene after integration. Finally, if the desired site lies within the genomic sequences of the adaptamers, it is necessary to synthesize a new adaptamer just outside of the ORF near that site.

The creation of de novo mutations within the ORF using adaptamer $A^{mut}$ or $B^{mut}$ always leads to the amplification of shortened gene fragments. The choice of which adaptamer to synthesize to create the mutation relies on the same criteria discussed above for fragmentation of large ORFs. Similarly, to avoid disruption of an essential gene when adaptamer $B^{mut}$ is used, an adaptamer $A^{pro}$ is necessary to create the amplified fragment. In addition, since the phenotype of the new mutation is unknown in most cases, it is advisable to design the alteration so that it can also be easily monitored physically (e.g., creation or destruction of a restriction enzyme site; generation of a deletion or an insertion). Another potential improvement of the de novo mutation method involves the length of the mutamer. Although it was shown that only 17 bp of homology upstream of the mutation was sufficient to obtain successful incorporation, the frequency of these events was low (25%). This frequency will likely increase with the length of the mutamer. However, it is important to simultaneously extend the length of the requisite *K. lactis* internal primer to avoid temperature differences for annealing during generation of the fusion fragment.

In this example, it was found that the frequency of integration into the genome is approximately 100-fold greater than that found with the other PCR-based allele replacement methods (Längle-Rouault and Jacobs 1995; Schneider, et al. 1995). This is likely due to the increased length of the homologous sequences used for targeting. Interestingly, 96% of the integrants exhibit cross-overs within the first 80 bp of the homologous sequences (Table P, line 3). It was also found that the presence of the 20 bp non-homologous tag, which is eliminated by recombination, does not interfere with the integration event. This is supported by the observation that a site 17 bp from the 5' end without the tag (sgs1-K706R) is incorporated as efficiently (25%) as a tagged-site 20 bp from the 5' end (rfa1-D228Y, 30%). This result agrees with those obtained with another PCR-based allele replacement method where it was shown that 22% of the transformants carried the alteration in both repeats when it was 24 bp from the ends of the fragment (Längle-Rouault and Jacobs 1995). Finally, although the frequency of integration of longer fragments increases 100-fold, it is still not as high as classical gene disruptions (Rothstein 1983). Perhaps the two fusion fragments used for the integration circularize since these two fragments contain homologous regions at both ends: the amplified allele and the *K. lactis* URA3 overlap. Such a circle would integrate into the genome at low efficiency and also decrease the total number of recoverable integration events by removing linear fragments from the "recombination pool."

In summary, the allele replacement method described in this paper is convenient for use in yeast since a set of adaptamers is commercially available for amplifying every ORF in the genome (Research Genetics). In addition, the *K. lactis* URA3 fragments can be synthesized in batches simplifying future fusions. Moreover, for the new adaptamers and mutamers that need to be synthesized, it was shown that only 15 bp are needed for priming most PCR amplifications. In principle these allele transfer methods can be applied to any organism that undergoes efficient homologous recombination, has genomic DNA sequence information available and has a suitable selectable/counterselectable marker.

Methods: Strains and Growth Conditions

Standard yeast genetic methods are employed for the analysis of strains and the preparation of the media (Sherman et al. 1986). The yeast strains used in this study are all derivatives of W303-1A unless otherwise noted. W303-1A is MATa ade2-1 can1-100 his3-11,15 leu2-3,112 trp1-1 ura3-1 (Thomas and Rothstein 1989). The kar1-1 strain was a gift from G. Fink (Conde and Fink 1976) and kar1-Δ15 strain was obtained from Phil Hieter (Spencer, et al. 1994). The *E. coli* strains are derivatives of TG1 (Sambrook, et al. 1989).

Plasmid Constructions

The *K. lactis* URA3 gene was amplified from a *Kluyveromyces lactis* strain by a PCR using adaptamers a and b of *K. lactis* URA3. The ends of the amplified product were made flush using T4 DNA polymerase (NE Biolabs) and pWJ716 was constructed by cloning the blunt-ended *K. lactis* URA3 fragment into the SmaI site of pRS414 plasmid (Sikorski and Hieter 1989).

Yeast Transformation

Yeast transformations were performed according to the high efficiency lithium acetate protocol without any modifications (Schiestl and Gietz 1989). 100 ng each of the two fusion fragments were used to transform yeast cells that routinely yield $10^5$ to $10^6$ transformants per µg of uncut circular DNA (pWJ716).

PCR

The primers used in this study are listed in Table Q. Standard conditions were used for PCR amplification (Erlich, 1989). To amplify two different but overlapping *K. lactis* URA3 fragments, 100 µl reactions were composed of 100 pg of pWJ716, 10 mM Tris, pH 8.3, 1.5 mM $MgCl_2$, 50 mM KCl, 0.2 mM each of dNTPs, and 1 µM primers and 5 units of Taq DNA polymerase (Boehringer Mannheim).

The rfa1-l-D228Y, kar1-1, and kar1-Δ5 mutations were amplified by colony PCR in 100 µl reactions from their respective strains. The above described PCR amplifications were performed on a Perkin-Elmer 9600 as follows: 3 min at 94° C., then a cycle of 94° C. for 30 sec, 54° C. for 30 sec and 72° C. for 1 minute repeated 35 times. The last cycle was followed by 5 minutes at 72° C. All PCR products were purified using GeneClean II™ (Bio101, Inc.).

The fusion fragments were generated by a modification of the PCR protocol described above. Specifically, 100 μl reactions were prepared from 10–25 ng each of the mutant allele and the appropriate *K. lactis* URA3 fragment, 10 mM Tris, pH 8.3, 1.5 mM MgCl$_2$, 50 mM KCl, 0.2 mM each of the dNTPs and 1 μM primers and 5 units of Taq polymerase (Boehringer Mannheim). The PCR amplifications were performed on a Perkin-Elmer 9600 using the following conditions: 3 min at 94° C., then 10 cycles of 94° C. for 30 sec, 54° C. for 15 sec and 72° for 4 min, followed by another 20 cycles of 94° C. for 30 sec, 60° C. for 15 sec and 72° C. for 4 minutes with addition of 30 sec at every cycle for the elongation step. The last cycle was followed by 5 minutes at 72° C. Again the PCR products were gel-purified from agarose gels using GeneClean II™ (Bio101, Inc.).

Colony PCR for detection of the rfa1-D228Y allele was performed using RFA1-2A and RFA1-3B primers (Smith and Rothstein 1995) under standard PCR conditions described above for amplifying the *K. lactis* URA3 fragments. The total volume of the PCR was 10 μl and cells that are barely visible on a toothpick were used as the template.

References

Bailis, A. M., and R. Rothstein. 1990. A defect in mismatch repair in *Saccharomyces cerevisiae* stimulates ectopic recombination between homeologous genes by an excision repair dependent process. *Genetics* 126: 535–547.

Barnes, W. M. 1992. The fidelity of Taq polymerase catalyzing PCR is improved by an N-terminal deletions *Gene* 112: 29–35.

Boeke, J. D., J. Trueheart, G. Natsoulis, and G. R. Fink. 1987. 5-Fluoroorotic acid as a selective agent in yeast molecular genetics. *Methods Enzymol.* 154: 164–175.

Conde, J., and G. R. Fink. 1976. A mutant of *Saccharomyces cerevisiae* defective for nuclear fusion. *Proc. Natl. Acad. Sci. U S A* 73: 3651–3655.

Erlich, H. A. 1989. PCR Technology: Principles and Applications for DNA Amplification, Stockton Press, N.Y.

Gangloff, S., J. P. McDonald, C. Bendixen, L. Arthur, and R. Rothstein. 1994. The yeast type I topoisomerase Top3 interacts with Sgs1, a DNA helicase homolog: a potential eukaryotic reverse gyrase. *Mol. Cell. Biol.* 14: 8391–8398.

Huxley, C., E. D. Green, and I. Dunham. 1990. Rapid assessment of *S. cerevisiae* mating type by PCR. *Trends Genet.* 6: 236.

Längle-Rouault, F., and E. Jacobs. 1995. A method for performing precise alterations in the yeast genome using a recyclable selectable marker. *Nucleic Acids Res* 23: 3079–3081.

Ling, M., F. Merante, and B. F. Robinson. 1995. A rapid and reliable DNA preparation method for screening a large number of yeast clines by polymerase chain reaction. *Nucl. Acids Res.* 23: 4924–4925.

Lu, J., J. R. Mullen, S. J. Brill, S. Kleff, A. M. Romeo, and R. Sternglanz. 1996. Human homologues of yeast helicase. *Nature* (London) 383: 678–679.

Ma, H., S. Kunes, P. J. Schatz, and D. Botstein. 1987. Plasmid construction by homologous recombination in yeast. *Gene* 58: 201–216.

Orr-Weaver, T. L., J. W. Szostak, and R. J. Rothstein. 1983. Genetic applications of yeast transformation with linear and gapped plasmids. *Methods Enzymol.* 101: 228–245.

Rothstein, R. J. 1983. One-step gene disruption in yeast. In Methods in Enzymology (ed. R. Wu, L. Grossman and K. Moldave), pp. 202–211. Academic Press, Inc., New York.

Sambrook, J., E. F. Fritsch, and T. Maniatis. 1989. Molecular cloning: A laboratory manual, Second edition. Cold Spring Harbor Laboratory Press, Cold Spring Harbor, N.Y.

Schiestl, R. H., M. Dominska, and T. D. Petes. 1993. Transformation of *Saccharomyces cerevisiae* with non-homologous DNA: illegitimate integration of transforming DNA into yeast chromosomes and in vivo ligation of transforming DNA to mitochondrial DNA sequences. *Mol. Cell. Biol.* 13: 2697–2705.

Schiestl, R. H., and R. D. Gietz. 1989. High efficiency transformation of intact yeast cells using single stranded nucleic acids as a carrier. *Curr. Genet.* 16: 339–346.

Schneider, B. L., W. Seufert, B. Steiner, Q. H. Yang, and A. B. Futcher. 1995. Use of Polymerase Chain Reaction Epitope Tagging for Protein Tagging in *Saccharomyces cerevisiae*. *Yeast* 11: 1265–1274.

Sherman, F., G. R. Fink, and J. B. Hicks. 1986. Methods in Yeast Genetics, Cold Spring Harbor Laboratory, Cold Spring Harbor, N.Y.

Shortle, D., J. E. Haber, and D. Botstein. 1982. Lethal disruption of the yeast actin gene by integrative DNA transformation. *Science* 217: 371–373.

Shuster, J. R., D. Moyer, and B. Irvine. 1987. Sequence of the *Kluyveromyces lactis* URA3 gene. *Nucl. Acids Res.* 15: 8573.

Sikorski, R. S., and P. Hieter. 1989. A system of shuttle vectors and yeast host strains designed for efficient manipulation of DNA in *Saccharomyces cerevisiae*. *Genetics* 122: 19–27.

Smith, J., and P. Modrich. 1997. Removal of polymerase-produced mutant sequences from PCR products [In Process Citation]. *Proc Natl Acad Sci U S A* 94: 6847–6850.

Smith, J., and R. Rothstein. 1995. A mutation in the gene encoding the *Saccharomyces cerevisiae* single-stranded DNA-binding protein Rfa1 stimulates a RAD52-independent pathway for direct-repeat recombination. *Mol. Cell. Biol.* 15: 1632– 1641.

Spencer, F., Y. Hugerat, G. Simchen, O. Hurko, C. Connelly, and P. Hieter. 1994. Yeast kar1 mutants provide an effective method for YAC transfer to new hosts. *Genomics* 22: 118–126.

Thomas, B. J., and R. Rothstein. 1989. The genetic control of direct-repeat recombination in Saccharomyces: the effect of rad52 and rad1 on mitotic recombination at GAL10, a transcriptionally regulated gene. *Genetics* 123: 725–738.

TABLE P

| Efficiency of allele transfer | |
|---|---|
| Position of the mutation from 5' end of homology | Percent with the mutation in both repeats |
| 21st bp | 30% (23) |
| 41st bp | 53% (32) |
| 81st bp | 96% (26) |
| 101st bp | 100% (20) |
| 682nd bp | 100% (25) |

The number in parentheses indicate the total number of transformants analyzed.

Table Q

Primers used in this study

| Name | Sequence |
|---|---|
| Adaptamer b for *K. lactis* URA3 | CATGGCAATTCCCGGGGATCGTGATTCTGGGTAGAAGATCG |
| Adaptamer a for *K. lactis* URA3 | CATGGTGGTCAGCTGGAATTCGATGATGTAGTTTCTGGTT |
| *K. lactis* internal 5' primer | CTTGACGTTCGTTCGACTGATGAGC |
| *K. lactis* internal 3' primer | GAGCAATGAACCCAATAACGAAATC |
| Adaptainer $A_{Rfa1}$ for RFA1 | AATTCCAGCTGACCACCATGATGAGCAGTGTTCAACTTTC |
| Adaptamer $B_{Rfa1}$ for RFA1 | GATCCCCGGGAATTGCCATGTTAAGCTAACAAAGCCTTGG |
| Adaptamer A1 for RFA1 | AATTCCAGCTGACCACCATGTATTCAATGTCAACTTCTTG |
| Adaptamer A21 for RFA1 | AATTCCAGCTGACCACCATGCAATCAAAGAGGTGATGG |
| Adaptamer A61 for RFA1 | AATTCCAGCTGACCACCATGAAGAGTTTCCTACAAGGGAG |
| Adaptainer A81 for RFA1 | AATTCCAGCTGACCACCATGAACGTTTGGACTATCAAAGC |
| Adaptamer $A_{Kar1}$ for KAR1 | AATTCCAGCTGACCACCATGATGAATGTAACTTCTCCAAA |
| Adaptamer $B_{Kar1}$ for KAR1 | GATCCCCGGGAATTGCCATGTTAAAACCTATAATACACAT |
| Adaptamer $A^{mut}$ for SGS1 | AATTCCAGCTGACCACCATGGATCTCTTTGCTATCAACTTC |
| Adaptamer $B_{Sgs1}$ for SGS1 | GATCCCCGGGAATTGCCATGCTTTCTTCCTCTGTAGTGACC |
| Mutamer for sgsl | GCCAACAGGGGTGGTAGATCTCTTTGCTATC |
| RFA1-2A | CAGAGCATCCAAATGAAACC |
| RFA1-3B | TTTGGATAATACCGAGGACG |

---

What is claimed is:

1. A method for generating a directed, recombinant fusion nucleic acid molecule capable of cross-over recombination which comprises:

(A) contacting
- (i) a first pair of single-stranded primers with a first strand and a second strand of a first nucleic acid molecule;
- (ii) a second and a third pair of primers with a second nucleic acid molecule having a first strand and a second strand, wherein the primers are suitable for use in a polymerase chain reaction, and
  - (a) the first primer of the first pair comprises a 3' sequence that is homologous to the first strand of the first nucleic acid molecule and a 5' sequence;
  - (b) the second primer of the first pair of primers comprises a 3' sequence that is homologous to the second strand of the first nucleic acid molecule and a 5' sequence;
  - (c) the first primer of the second pair of primers comprises a sequence that is homologous to the second strand of the second nucleic acid molecule;
  - (d) the second primer of the second pair of primers comprises a 3' sequence that is homologous to the first strand of the second nucleic acid molecule and a 5' sequence that is complementary to the 5' sequence of the first primer of the first pair of primers;
  - (e) the first primer of the third pair of primers comprises a 5' sequence complementary to the 5' sequence of the second primer of the first pair of primers and a 3' sequence homologous to the second strand of the second nucleic acid molecule, and
  - (f) the second primer of the third pair of primers comprises a sequence that is homologous to the first strand of the second nucleic acid molecule;

(B) amplifying (1) the first nucleic acid molecules with the first pair of primers and (2) the second nucleic acid molecule with the second and third pairs of primers, so as to generate at least one linear double-stranded nucleic acid product from each reaction;

(C) denaturing the products from step (B) so as to obtain single-stranded products;

(D) contacting the single-stranded products from step (C) with the first primer of the second set of primers and the second primer from the third set of primers, under suitable hybridization conditions, and (E) amplifying the the single-stranded products from step (D) under suitable amplification conditions, so as to generate a fusion nucleic acid molecule capable of cross-over recombination.

2. The method of claim 1, wherein cross-over recombination occurs in an appropriate host cell.

3. The method of claim 2, wherein the host cell comprises a yeast cell, a mammalian cell, an *E.coli cell*, a eukaryotic cell, a prokaryotic cell, a plant cell, an insect cell, a slime mold cell.

4. The method of claim 1, wherein the first nucleic acid molecule comprises a cDNA molecule, a genomic nucleic acid molecule, a mitochondrial nucleic acid molecule, a chromosomal nucleic acid molecule, a synthetic nucleic acid molecule or an extra-chromosomal nucleic acid molecule.

5. The method of claim 1, wherein the first nucleic acid molecule is derived from an mRNA, a single-stranded DNA, or a single-stranded cDNA.

6. The method of claim 1, wherein the second nucleic acid molecule comprises a replicable vector.

7. The method of claim 6, wherein the replicable vector comprises a retroviral vector, a phage vector, an expression vector, a self-replicating vector, a viral vector, a plasmid vector, a phagemid vector, or a YAC vector.

8. The method of claim 1, wherein the fusion nucleic acid comprises an insertion, a deletion a duplication or a mutation in the fusion nucleic acid molecule.

9. A method for generating a directed, recombinant nucleic acid library which comprises:

(A) contacting
- (i) a first pair of single-stranded primers with a first strand and a second strand of a first nucleic acid molecule;
- (ii) a second and a third pair of primers with a second nucleic acid molecule having a first strand and a second strand, wherein the primers are suitable for use in a polymerase chain reaction, and
  - (a) the first primer of the first pair comprises a 3' sequence that is homologous to the first strand of the first nucleic acid molecule and a 5' sequence;
  - (b) the second primer of the first pair of primers comprises a 3' sequence that is homologous to the second strand of the first nucleic acid molecule and a 5' sequence;
  - (c) the first primer of the second pair of primers comprises a sequence that is homologous to the second strand of the second nucleic acid molecule;
  - (d) the second primer of the second pair of primers comprises a 3' sequence that is homologous to the first strand of the second nucleic acid molecule and a 5' sequence that first primer of the first pair of primers;

(e) the first primer of the third pair of primers comprises a 5' sequence complementary to the 5' sequence of the second primer of the first pair of primers and a 3' sequence homologous to the second strand of the second nucleic acid molecule, and (f) the second primer of the third pair of primers comprises a sequence that is homologous to the first strand of the second nucleic acid molecule;

(B) amplifying (1) the first nucleic acid molecule with the first pair of primers and (2) the second nucleic acid molecule with the second and third pairs of primers, so as to generate at least one linear double-stranded nucleic acid product from each reaction;

(C) denaturing the products from step (B) so as to obtain single-stranded products;

(D) contacting the single-stranded products from step (C) with the first primer of the second set of primers and the second primer from the third set of primers under suitable hybridization conditions, and (E) amplifying the the single-stranded products from step (D) so as to generate a fusion nucleic acid molecule capable of cross-over recombination under suitable amplification conditions;

(F) mixing the fusion nucleic acid molecule with the second nucleic acid molecule under suitable recombination conditions so as to generate a directed, recombinant nucleic acid library. recombinant nucleic acid library.

10. The method of claim 9, wherein the library is a two-hybrid library, an interaction library, a receptor library, a whole animal library, a tagged library, a chimeric library, a gene fusion library, a promoter trap library, an expression library, or a mutagenesis library.

11. The method of claim 9, wherein the cross-over recombination occurs in an appropriate host cell.

12. The method of claim 11, wherein the host cell comprises a yeast cell, a mammalian cell, an *E.coli* cell, a eukaryotic cell, a prokaryotic cell, a plant cell, an insect cell, a slime mold cell.

13. The method of claim 9, wherein the first nucleic acid molecule comprises a cDNA molecule, a genomic nucleic acid molecule, a mitochondrial nucleic acid molecule, a chromosomal nucleic acid molecule, a synthetic nucleic acid molecule or an extra-chromosomal nucleic acid molecule.

14. The method of claim 9, wherein the first nucleic acid molecule is derived from an mRNA, a synthetic nucleic acid, a single-stranded DNA, or a single-stranded cDNA.

15. The method of claim 9, wherein the second nucleic acid molecule comprises a replicable vector.

16. The method of claim 15, wherein the replicable vector comprises a retroviral vector, a phage vector, an expression vector, a self-replicating vector, a viral vector, a plasmid vector, a phagemid vector, or a YAC vector.

17. A kit for generating a fusion nucleic acid based library which comprises:

(a) a plurality of the adapted nucleic acid molecule primers of claim 9;

(b) reagents suitable to carry out a plurality of polymerase chain reactions, and (c) a replicable vector suitable for recombination.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

CGAGGATCCG AATTCCAGCA AGAATTCGGC ACGAGG       36

(2) INFORMATION FOR SEQ ID NO: 2:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 2:

CGAGGATCCG AATTCCAGCC AAGAATTCGG CACGAGG       37

(2) INFORMATION FOR SEQ ID NO: 3:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: DNA (genomic)

-continued (xi) SEQUENCE DESCRIPTION: SEQ ID NO: 3:

CGAGGATCCG AATTCCAGGC CAAGAATTCG GCACGAGG            38

(2) INFORMATION FOR SEQ ID NO: 4:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 4:

GTTGAAGTGA ACTTGCGGGA CGTTGTAAAA CGACGG            36